United States Patent
Northcutt et al.

(10) Patent No.: US 9,364,267 B2
(45) Date of Patent: Jun. 14, 2016

(54) DYNAMIC AND NON-DYNAMIC INTERSPINOUS FUSION IMPLANT AND BONE GROWTH STIMULATION SYSTEM

(71) Applicant: Aurora Spine, LLC, Carlsbad, CA (US)

(72) Inventors: Trent James Northcutt, Oceanside, CA (US); Laszlo Garamszegi, Mission Viejo, CA (US)

(73) Assignee: AURORA SPINE, INC., Carlsbad, CA (US)

( * ) Notice: Subject to any disclaimer, the term of this patent is extended or adjusted under 35 U.S.C. 154(b) by 332 days.

(21) Appl. No.: 13/865,155

(22) Filed: Apr. 17, 2013

(65) Prior Publication Data
US 2013/0296940 A1    Nov. 7, 2013

Related U.S. Application Data

(60) Provisional application No. 61/625,626, filed on Apr. 17, 2012, provisional application No. 61/640,163, filed on Apr. 30, 2012, provisional application No. 61/674,807, filed on Jul. 23, 2012, provisional application No. 61/716,779, filed on Oct. 22, 2012, provisional application No. 61/778,627, filed on Mar. 13, 2013.

(51) Int. Cl.
*A61F 2/44* (2006.01)
*A61B 17/70* (2006.01)
*A61F 2/28* (2006.01)

(52) U.S. Cl.
CPC ......... *A61B 17/7062* (2013.01); *A61B 17/7008* (2013.01); *A61B 17/7067* (2013.01); *A61B 17/7068* (2013.01); *A61B 17/7055* (2013.01); *A61F 2002/2821* (2013.01)

(58) Field of Classification Search
CPC ........... A61B 17/7059; A61B 17/7064; A61B 17/7067; A61B 17/7065; A61B 17/7068; A61B 17/7055; A61F 2002/2821
USPC ................................. 606/246–279, 280–299; 623/17.11–17.16
See application file for complete search history.

(56) References Cited

U.S. PATENT DOCUMENTS 5,876,404 A    3/1999  Zucherman et al.
6,048,342 A    4/2000  Zucherman et al.

(Continued)

*Primary Examiner* — Mary Hoffman
*Assistant Examiner* — Tara R Carter
(74) *Attorney, Agent, or Firm* — Hybrid Law Group PC

(57) ABSTRACT

An interspinous fusion device is described. The interspinous fusion device includes a spacer member and an anchor member. The spacer member has a ring with two or more anchor assemblies projecting laterally from substantially opposite sides of the spacer member ring. The spacer member further has a first zip lock flange and a second zip lock flange, each of the first and second zip lock flanges extends transversely from the spacer member ring wherein each of the first and second zip lock flanges each comprises a series of teeth protruding from it. The anchor member has a ring with two or more anchor assemblies projecting laterally from substantially opposite sides of the anchor member ring. The anchor member further has a barrel extending transversely from the anchor member ring. The barrel comprises a first column of recesses adapted to mate with the teeth of the first zip lock flange and a second column of recesses adapted to mate with the teeth of the second zip lock flange. The spacer member is adapted to slide over the barrel of the anchor member such that the series of teeth of the first zip lock flange mates with the recesses in the first column of recesses of the barrel, and the series of teeth of the second zip lock flange mates with the recesses in the second column of recesses of the barrel to secure the spacer member to the anchor member.

4 Claims, 17 Drawing Sheets

(56) References Cited

U.S. PATENT DOCUMENTS

| | | | |
|---|---|---|---|
| 6,068,630 | A | 5/2000 | Zucherman et al. |
| 6,152,926 | A | 11/2000 | Zucherman et al. |
| 6,183,471 | B1 | 2/2001 | Zucherman et al. |
| 6,190,387 | B1 | 2/2001 | Zucherman et al. |
| 6,235,030 | B1 | 5/2001 | Zucherman et al. |
| 6,432,108 | B1 * | 8/2002 | Burgess et al. ............... 606/252 |
| 6,695,842 | B2 | 2/2004 | Zucherman et al. |
| 7,048,736 | B2 | 5/2006 | Robinson et al. |
| 7,635,378 | B2 | 12/2009 | Zucherman et al. |
| 7,727,233 | B2 | 6/2010 | Blackwell et al. |
| 7,879,073 | B2 | 2/2011 | Pasquet et al. |
| 8,002,805 | B2 | 8/2011 | Le Couedic et al. |
| 8,114,132 | B2 | 2/2012 | Lyons et al. |
| 8,123,782 | B2 | 2/2012 | Altarac et al. |
| 8,128,659 | B2 | 3/2012 | Ginsberg et al. |
| 8,128,661 | B2 | 3/2012 | Zucherman et al. |
| 8,206,420 | B2 | 6/2012 | Patel et al. |
| 8,231,656 | B2 | 7/2012 | Lee et al. |
| 8,241,330 | B2 | 8/2012 | Lamborne et al. |
| 8,262,697 | B2 | 9/2012 | Kirschman et al. |
| 8,636,771 | B2 * | 1/2014 | Butler et al. .................. 606/248 |
| 2007/0162001 | A1 | 7/2007 | Chin et al. |
| 2007/0179500 | A1 | 8/2007 | Chin et al. |
| 2007/0233082 | A1 | 10/2007 | Chin et al. |
| 2008/0177326 | A1 | 7/2008 | Thompson et al. |
| 2010/0087860 | A1 | 4/2010 | Chin et al. |
| 2010/0125301 | A1 * | 5/2010 | Kinmon et al. ................ 606/300 |
| 2010/0222817 | A1 | 9/2010 | Perez-Cruet et al. |
| 2011/0022090 | A1 | 1/2011 | Gordon et al. |
| 2011/0054531 | A1 | 3/2011 | Lamborne et al. |
| 2011/0066186 | A1 * | 3/2011 | Boyer et al. .................. 606/249 |
| 2011/0098745 | A1 | 4/2011 | Liu et al. |
| 2011/0166600 | A1 | 7/2011 | Lamborne et al. |
| 2011/0172720 | A1 | 7/2011 | Metcalf, Jr. et al. |
| 2011/0319936 | A1 | 12/2011 | Gordon et al. |

* cited by examiner

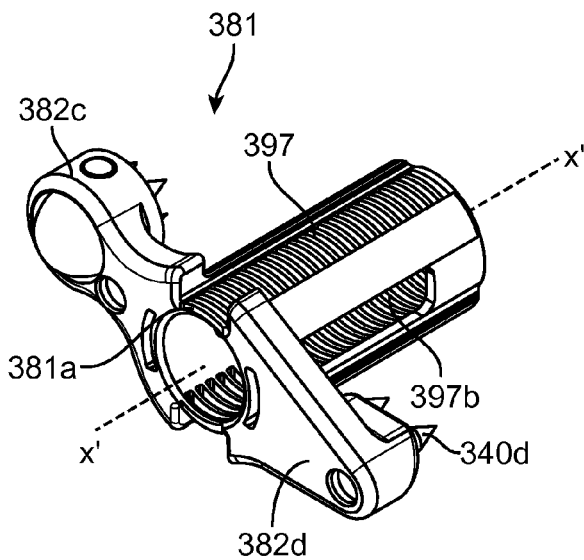
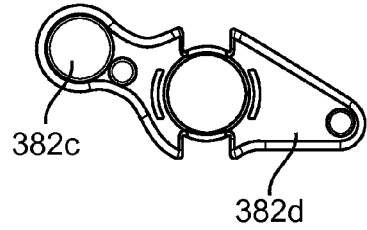
FIG. 13a
FIG. 13b
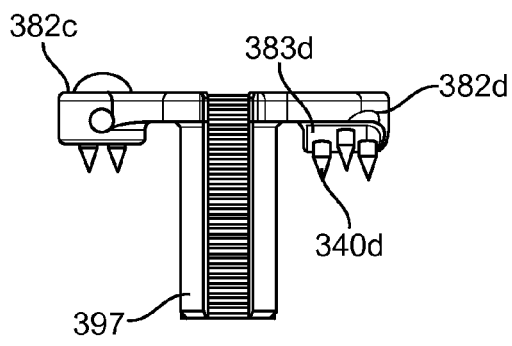
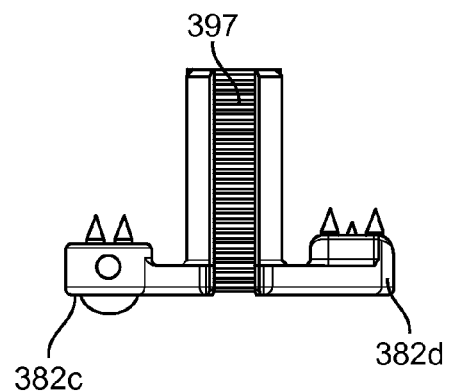
FIG. 13c
FIG. 13d
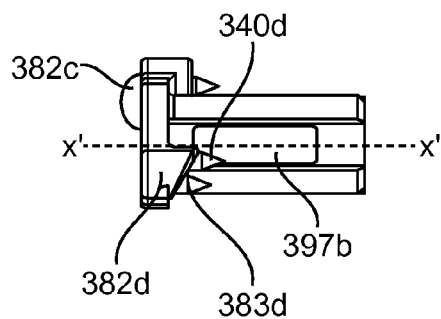
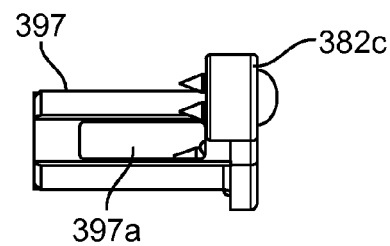
FIG. 13e
FIG. 13f

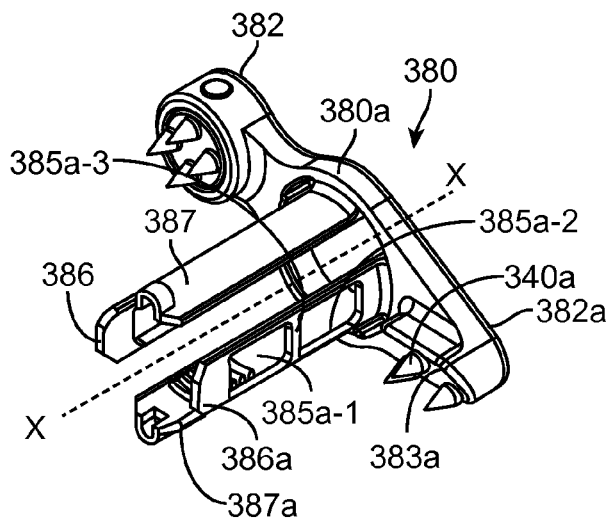
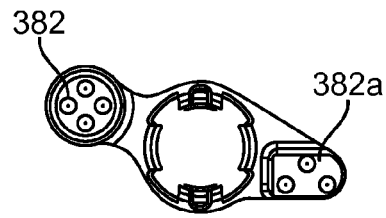
FIG. 14a
FIG. 14b
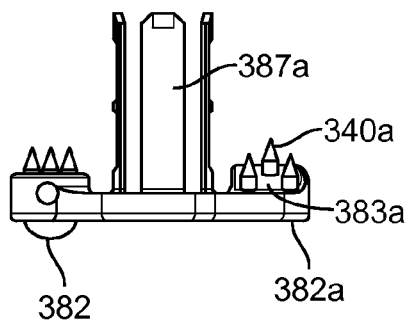
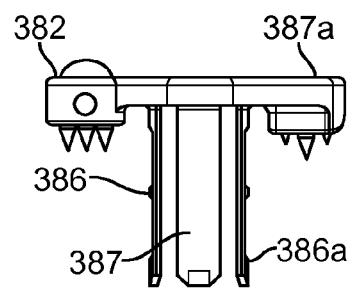
FIG. 14c
FIG. 14d
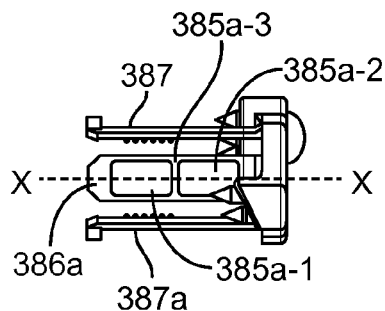
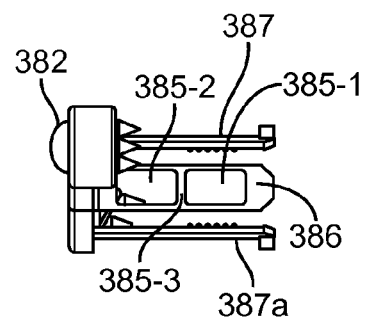
FIG. 14e
FIG. 14f

DYNAMIC AND NON-DYNAMIC INTERSPINOUS FUSION IMPLANT AND BONE GROWTH STIMULATION SYSTEM

RELATED APPLICATIONS

This application claims priority from the following U.S. Provisional Patent Applications, all of which are incorporated herein by reference in their entirety: 61/625,626 filed Apr. 17, 2012, 61/640,163 filed Apr. 30, 2012, 61/674,807 filed Jul. 23, 2012, 61/716,779 filed Oct. 22, 2012, and 61/778,627 filed Mar. 13, 2013.

BACKGROUND

This invention relates generally to the field of spinal fusion surgery and more specifically to interspinous fusion implants and bone growth stimulation systems.

In 1986, the first interspinous device was introduced in Europe. It was the first dynamic stabilization system and consequently has the longest history at present. The device's original design was a titanium blocker that was inserted between adjacent processes and held in place with a polyester band wrapped around the spinous process above and below the blocker. After this first-generation device showed positive results, a second generation of interspinous implants were developed. The primary change was in the material used for the interspinous spacer. It was changed from titanium to polyetheretherketone (PEEK), a strong, plastic-like polymer that has more elasticity and is therefore less rigid than the previously used material. The implant has notches that fit the physiological shape of the lumbar spine.

Several devices currently exist that can be inserted between the spinous apophysis. Said devices have their antecedents in bone grafts placed between the spines more than fifty years ago. They were H-shaped and placed so that their ends surrounded the spines and their horizontal part was located between said spines in order to diminish the mobility among the vertebrae and achieve its final fusion. Likewise, there exist antecedents related to vertebral fusion which used different bow types, mostly metal bows to be linked to the spinous apophysis so that they become immobilized.

Newer technologies also exist that prohibit both flexion and compression between successive spinous processes. These devices are inserted between the spinous processes and contain barrel-like objects that maintain a space between the spinous processes thus prohibiting compression, while also containing successive plates with spikes that bore into successive spinal processes thus prohibiting flexion.

The problem with all of the known devices is associated with wear and tear. Interspinous implants are meant to be long-term solutions that remain implanted for preferably the life of the subject who is treated with them. With life expectancy of people in developed countries exceeding 80 years of age and many people now living actively into their 90s, these devices must maintain their functional integrity and must not fail for decades. Unfortunately, many of the current implants are prone to failure due to their design. What is needed are implants that remain firmly in place and maintain their functional integrity and are unlikely to suffer a mechanical failure for the life of the recipient of the implants.

Another problem is that current implants have barrels that do not allow for small amounts of flexion or compression between spinous processes. Yet, the human body is dynamic and the vertebral column is adapted to allow flexion and compression between spinous processes. This is necessary to protect adjacent discs from degeneration. Thus, once implanted, prior devices do not allow for any relative movement between successive spinous processes. What's needed are devices that allow for small amounts of controlled flexion and compression between successive spinous processes while maintaining their functional integrity and not being prone to failure.

Yet another problem is that most implants that prohibit compression and flexion require set screws and drivers to fix the components of the implants to the bone and fix the parts of the implant firmly in place relative to one another. This requires extra space to work in order to screw and unscrew. In addition, the single point of a set screw is tasked with maintaining the orientation of the parts of the device for as long as the device is in the body. All of the forces that pull and push the parts of the device toward and away from one another converge on the single set screw point that is tasked with maintaining the functional integrity of the device and prevent its failure. What is needed are devices that remain their functional integrity for long periods of time and are not prone to the limitations of using set screws.

Also lacking in the field are interspinous implants adapted for the cervical spine that don't require pedicle screws and rods or fusion plates and are modular and adaptable to the specific patient anatomy.

Current devices are also dumb in the sense that they have no capability to record local data and transmit it to an external device where the data can be processed and analyzed by healthcare professionals as part of ongoing patient care. What's needed are interspinous implants that can store and/or obtain information about the implant and its environment, such as the stresses on the implant, whether the implant has moved over time, whether the parts of the implant have become dislodged from one another or have loosened, the date the implant was implanted, and patient identification information, and so on. This will allow for healthcare providers to better manage the care of patients who have such devices implanted in the spinal column without having to resort to surgical intervention to determine the status of the implants.

Current interspinous devices lack any ability to promote bone growth. What's needed are orthopedic implants that can be activated by an external device to stimulate and promote bone growth and fusion when fusion is desired. No such devices exist at the present time, and yet they are needed to promote healing and reduce the time it takes for fusion between successive vertebrae to occur.

SUMMARY

One object of the invention is to provide a better interspinous implant that allows controlled, dynamic movement of vertebrae until fusion occurs while using a one-step, easy to install friction-lock mechanism with a zipping action. This type of locking mechanism eliminates the need for screws and screw drivers for securing implant components to bone.

Another object of the invention is to provide a device in which loosening of screws or migration of the implant cannot occur since the mechanism is a compressible friction-lock system with a zipping action and multiple engagement points.

Another object of the invention is to provide a spinal fusion implant that is dynamic, therefore preventing spinal discs at the fusion site from being completely immobile and allowing some controlled movement between successive interspinous processes.

Another object of the invention is to provide a spinal fusion implant that is dynamic, therefore allowing controlled load sharing and movement of discs above and below fusing vertebrae, thus protecting discs above and below fusing vertebras from degenerating over time as a result of the fusion.

Yet another object of the invention is to provide a spinal fusion implant that can be implanted in a downward direction to attach in a parallel fashion to upward protruding walls of spinous processes.

Still yet another object of the invention is to provide a spinal fusion implant that can be implanted in an upward direction to attach to the angled root of spinous processes.

Another object of the invention is to provide a spinal fusion implant that can be implanted in an upward or downward direction, depending on quality and bone volume required for the implantation.

Another object of the invention is to provide a spinal fusion implant which requires a small incision for implantation for reduced trauma to the patient.

A further object of the invention is to provide a spinal fusion implant that can be safely adjusted and compressed or decompressed safely when necessary any time after completion of surgery thru a small percutaneous opening.

Still yet another objective of the invention is to provide a dynamic spinal fusion implant where the dynamic feature of the implant can be locked when needed, and the locking can be fully reversed when necessary so that the implant becomes dynamic again, i.e. an implant that can be dynamic or non-dynamic depending on the need of the patient at the time.

In various embodiments, the spinal fusion implant devices described herein can be manufactured from implantable metal, plastic or reinforced plastic. They can also be manufactured from metal reinforced plastic making the implant body conductive to carry electrical signals or current, or from entirely conductive material to carry electrical signals or current. They can also be manufactured with a surface made of pyrolitic carbon over a graphite core.

In one embodiment, the devices described herein can carry electrical signals or current for the promotion or stimulation of bone growth. Such devices can serve as electrical or magnetic bone growth stimulators. In another embodiment, they can be activated to emit magnetic energy by receiving wireless signals that activate them to emit magnetic energy.

Another object of the invention is to provide a spinal fusion implant built together with a micro-electro-mechanical system chip (or MEMS chip) for the transmission of clinically useful patient information to an external reader. Such a chip can also continuously monitor a patient after surgery or be activated to gather local data and save it in memory or transmit it upon obtaining the data.

In one embodiment, an interspinous fusion device is described. The interspinous fusion device includes a spacer member and an anchor member. The spacer member has a ring with two or more anchor assemblies projecting laterally from substantially opposite sides of the spacer member ring. The spacer member further has a first zip lock flange and a second zip lock flange, each of the first and second zip lock flanges extends transversely from the spacer member ring wherein each of the first and second zip lock flanges each comprises a series of teeth protruding from it. The anchor member has a ring with two or more anchor assemblies projecting laterally from substantially opposite sides of the anchor member ring. The anchor member further has a barrel extending transversely from the anchor member ring. The barrel comprises a first column of recesses adapted to mate with the teeth of the first zip lock flange and a second column of recesses adapted to mate with the teeth of the second zip lock flange. The spacer member is adapted to slide over the barrel of the anchor member such that the series of teeth of the first zip lock flange mates with the recesses in the first column of recesses of the barrel, and the series of teeth of the second zip lock flange mates with the recesses in the second column of recesses of the barrel to secure the spacer member to the anchor member.

In accordance with another embodiment, an interspinous fusion device has a first member and a second member. The first member has a set of first lateral spinous process attachment arms and a first locking member transverse to the first lateral spinous process attachment arms, wherein the locking member comprises a row of zip-locking teeth. The second member comprising a set of second lateral spinous process attachment arms and a second locking member transverse to the second lateral spinous process attachment arms, wherein the second locking member comprises a row of zip-locking recesses that are sized to receive the zip-locking teeth of the first member and wherein the first and second members can be reversibly locked together when they mate.

In accordance with another embodiment, an orthopedic implant is described. The orthopedic implant has a surface made of pyrolitic carbon, wherein the orthopedic implant is capable of receiving a wireless signal from an external transmitter and emitting a magnetic field that stimulates bone growth in an area adjacent the implant.

In accordance with another embodiment, a kit for orthopedic surgical procedures is provided. The kit includes one or more orthopedic implants. The one or more orthopedic implants have a surface made of pyrolitic carbon. The orthopedic implants are capable of receiving a wireless signal from an external transmitter and emitting a magnetic field that stimulates bone growth in an area adjacent the implant. The kit also includes natural or synthetic bone matrix and a wireless signal transmitter that is capable of transmitting a wireless signal to the one or more orthopedic implants.

In yet another embodiment, a cervical implant is described. The cervical implant has a first barrel, a second barrel, and one or more plates that connect the first barrel to the second barrel. The first barrel has one or more hooks engaged to it, wherein the one or more hooks are movable relative to the first barrel. The second barrel also has one or more hooks engaged to it, wherein the one or more hooks of the second barrel are movable relative to the second barrel. The hooks can be rotated concentrically about the barrels.

In accordance with another embodiment, a modular cervical implant system is described. The modular cervical implant system has a first barrel, a second barrel, a first pair of plates, one or more additional barrels and a second or more pair of plates corresponding to the number of additional barrels. The first barrel has one or more hooks engaged to it, wherein the one or more hooks are movable relative to the first barrel. The second barrel also has one or more hooks engaged to it, wherein the one or more hooks of the second barrel are movable relative to the second barrel. The first pair of plates connect the first barrel to the second barrel. The one or more additional barrels each also has one or more hooks engaged to it, wherein the one or more hooks of the one or more additional barrels are movable relative to its respective barrel. Each pair of the second or more pair of plates connects one of the additional barrels to the first or the second barrel or to another of the additional barrels.

In accordance with another embodiment, an interspinous fusion system is described. The interspinous fusion system has a number of interspinous fusion devices and a pair of rods that connects the interspinous fusions devices to one another. The first of the pair of rods can be connected to a first member of each of the series of interspinous fusion devices and the second of the pair of rods can be connected to a second member of each of the series of interspinous fusion devices.

Other objects and advantages of the present invention will become apparent from the following descriptions, taken in connection with the accompanying drawings, wherein, by way of illustration and example, various embodiments of the present invention are disclosed.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

FIG. 8c is an exploded view of the multiple successive interspinous implants depicted in FIG. 8a.

FIG. 10b is a side view of the modular cervical interspinous implant system depicted in FIG. 10a.

FIG. 10c is an isometric view of the modular cervical interspinous implant system depicted in FIG. 10a.

FIG. 12A is an isometric view. FIG. 12b is a top view. FIG. 12c is a view of one end of the device, and FIG. 12d is a view of the opposite end of the device. FIG. 12e is a view of the right side of the device, and FIG. 12f is a view of the left side of the device.

FIGS. 13a-13f are various views of the left component of the interspinous implant depicted in FIGS. 12a-12f. FIG. 13a is an isometric view. FIG. 13b is a view of the left side of the component. FIG. 13c is a bottom view of the component. FIG. 13d is a top view of the component. FIG. 13e is a view of one end of the component, and FIG. 13f is a view of the opposite end of the component.

FIGS. 14a-14f are various views of the right component of the interspinous implant depicted in FIGS. 12a-12f. FIG. 14a is an isometric view. FIG. 14b is a view of the left side of the component. FIG. 14c is a bottom view of the component. FIG. 14d is a top view of the component. FIG. 14e is a view of one end of the component, and FIG. 14f is a view of the opposite end of the component.

DETAILED DESCRIPTION

Figure 1:
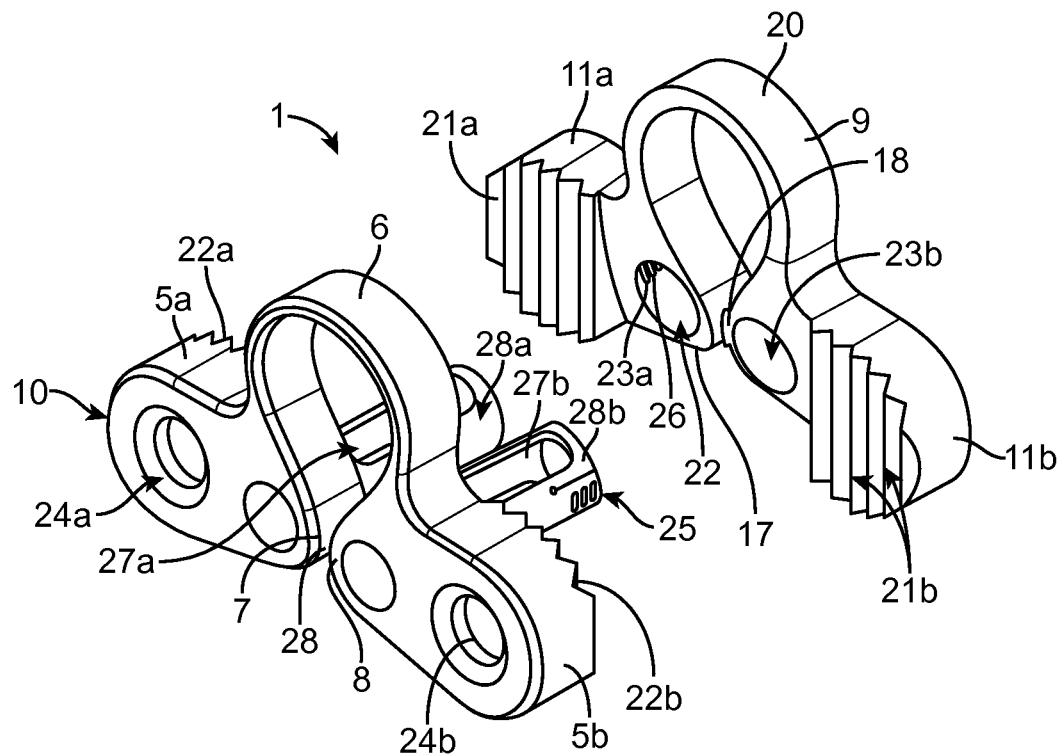
FIG. 1 is an exploded isometric view of an interspinous implant in accordance with one embodiment.

Exemplary embodiments of the invention are shown in the accompanying figures. In accordance with one embodiment, FIG. 1 shows one embodiment of a dynamic interspinous implant 1 made of two separate but interlocking components, male component 10 and female component 20. The two components 10 and 20 are shown in an exploded view in FIG. 1, but they are locked together when implanted as described further herein. Male component 10 has two arms projecting up and down respectively from a central loop 6. The first arm 5a projects in an upward or superior direction from loop 6, and the second arm 5b projects in a downward or inferior direction from loop 6. Both arms 5a and 5b are integrally formed in a unibody construction with loop 6 and are connected to one another through loop 6. The lower portion 7 of arm 5a is in close proximity to the upper portion 8 of arm 5b. In its resting state when no forces are exerted on male component 10, the distance between lower portion 7 and upper portion 8 is between about 1.0 mm and 10.0 mm, so that the distance can be about 1.0 mm, 1.5 mm, 2.0 mm, 2.5 mm, 3.0 mm, 3.5 mm, 4.0 mm, 4.5 mm, 5.0 mm, 5.5 mm, 6.0 mm, 6.5 mm, 7.0 mm, 7.5 mm, 8.0 mm, 8.5 mm, 9.0 mm, 9.5 mm, 10.0 mm, or 10.5 mm. The loop 6 is semi-rigid and can be compressed or flexed. When the loop 6 is squeezed arms 5a and 5b are compressed toward each other. At full compression, lower portion 7 comes into contact with upper portion 8 so that no further compression can be achieved. Arms 5a and 5b have compression recesses 24a and 24b. Compression recesses 24a and 24b receive a compression tool that is used to squeeze male component 10 and female component 20 toward one another. Although not visible in FIG. 1, female component 20 has corresponding compression recesses on outer sides of arms 11a and 11b that receive a compression tool as well. The inner sides of arms 5a and 5b form a surface having serrated teeth 22a and 22b respectively to fixedly engage with bone of the spinous process. Alternatively, the inner sides of arms 5a and 5b can have spikes that engage the bone. Projecting transversely from the inner side of the lower portion 7 is a first locking barrel 28a that corresponds and mates with zip-lock recess 23a of female component 20. Projecting transversely from the inner side of the upper portion 8 is a second locking barrel 28b that corresponds and mates with zip lock recess 23b of female component 20. Barrels 28a and 28b have bone graft windows 27a and 27b respectively. These windows allow for bone to grow through them and allow for adjacent vertebrae to fuse with one another when the interspinous implant 1 is implanted between spinous processes.

Across from male component 10 is female component 20. Female component 20 has two arms projecting up and down respectively from a central loop 9. The first arm 11*a* projects in an upward or superior direction from loop 9, and the second arm 11*b* projects in a downward or inferior direction from loop 9. Both arms 11*a* and 11*b* are integrally formed in a unibody construction with loop 9 and are connected to one another through loop 9. The lower portion 17 of arm 11*a* is in close proximity to the upper portion 18 of arm 11*b*. Just as with male component 10, in its resting state when no forces are exerted on female component 20, the distance between lower portion 17 and upper portion 18 is between about 1.0 mm and 10.0 mm, so that the distance can be about 1.0 mm, 1.5 mm, 2.0 mm, 2.5 mm, 3.0 mm, 3.5 mm, 4.0 mm, 4.5 mm, 5.0 mm, 5.5 mm, 6.0 mm, 6.5 mm, 7.0 mm, 7.5 mm, 8.0 mm, 8.5 mm, 9.0 mm, 9.5 mm, 10.0 mm, or 10.5 mm. The loop 6 is semi-rigid and can be compressed or flexed. When the loop 9 is squeezed arms 11*a* and 11*b* are compressed toward each other. At full compression, lower portion 17 comes into contact with upper portion 18 so that no further compression can be achieved. Thus, loop 6 is opposite to and corresponds with loop 9. Arm 11*a* is opposite to and corresponds with arm 5*a*. Arm 11*b* is opposite to and corresponds with arm 5*b*. The inner sides of arms 11*a* and 11*b* form a surface having serrated teeth 21*a* and 21*b* respectively to fixedly engage with bone of the spinous process. Alternatively, the inner sides of arms 11*a* and 11*b* can have spikes that engage the bone.

The juncture between the lamina and the spinous process is curved. The spinous process itself is not uniform in thickness and perfectly flat on both sides. It tends to bow in and out. To account for the curvature of the spinous process and the lamina, the inner surface of the loops 6 and 9 can be at an angle relative to the arms 5*a* and 5*b* and 11*a* and 11*b* respectively as shown in FIG. 1. Thus, when the serrated teeth 21*a*, 21*b*, 22*a*, and 22*b* have dug into the bone, the inner surfaces of the loops 6 and 9 rest flush against the outer sides of the successive spinous processes.

Male component 10 and female component 20 mate with one another in the following manner. As the two are brought toward one another, barrels 28*a* and 28*b* slide into zip-lock recesses 23*a* and 23*b* respectively. Inside of recesses 23*a* and 23*b* are zip-locking teeth 26 (each recess can have the zip-locking teeth although they are only visible in recess 23*a* in the view shown in FIG. 1). Zip locking teeth 26 can encircle the entire inner radius of the recess or they can form an arc that does not completely encircle the recess as shown in FIG. 1. In yet another embodiment, there can be two or multiple sets of teeth opposing each other within the recesses 23*a* and 23*b*. Teeth 26 protrude out from the surface of the recesses 23*a* and 23*b* toward the center of each recess. Each tooth of the series of zip lock teeth 26 can form a top angled sliding face and a back locking ridge. The sliding face is angled to allow teeth 26 to slide forward and mate with the zip lock holes 25 that are on the surface of the barrels 28*a* and 28*b*. The back locking ridge of teeth 26 can form a substantially 90° angle (or alternatively an acute angle) with the inner surface of the recesses 23*a* and 23*b*.

When the barrels 28*a* and 28*b* slide into recesses 23*a* and 23*b*, the teeth 26 slide over the outer surface of the barrels 28*a* and 28*b* and into the holes 25 on the barrel that are sized and shaped to receive the teeth 26. Only three holes 25 are shown in FIG. 1, but there can be more than that number of holes or fewer. In one embodiment, there are 4 holes. In other embodiments, there are 5, 6, 7, 8, 9, 10 or more holes on each barrel to receive between 1 and 10 teeth from each zip-lock recess 23*a* and 23*b*. When teeth 26 engage with holes 25, the male component 10 and female component 20 become locked to one another. The distance between the male component 10 and female component 20 can be adjusted by sliding the barrels 28*a* and 28*b* further into recesses 23*a* and 23*b*.

Male and female components 10 and 20 mate with one another to form a single interspinous implant 1 that not only separates two adjacent spinous processes from one another at a predetermined distance, but keeps them locked with respect to one another as a result of the penetration of the spinous processes by the serrated teeth 21*a*, 21*b*, 22*a*, and 22*b*. The opposing loops 6 and 9 prevent extension between adjacent spinous processes, while the serrated teeth 21*a*, 21*b*, 22*a*, and 22*b* prevent flexion between two adjacent spinous processes, except for a limited amount due to the dynamic nature of the interspinous implant 1 resulting from the flexible loops 6 and 9 that allow the lower portions 7 and 17 and upper portions 8 and 18 to move toward and away from one another respectively.

In one method of implantation, the assembled interspinous implant 1 can be inserted between two spinous processes of adjacent vertebrae in an anterior to posterior direction after severing spinous ligaments to remove them from the path of implantation. In another method of implantation, no spinous ligaments are severed and the male and female components 10 and 20 are separated and can each individually be inserted from opposing lateral directions toward each other anterior to the undisturbed spinous ligaments. In either case, once the two components are on opposite sides of successive spinous processes, male and female components 10 and 20 are squeezed or pushed toward one another with a compression tool until the serrated teeth 21*a* and 22*a* penetrate the outer sides of a superior spinous process while the serrated teeth 21*b* and 22*b* penetrate the outer sides of the spinous process just inferior to the superior spinous process penetrated by the teeth 21*a* and 22*a*. With the penetration of the teeth the interspinous implant 1 prohibits uncontrolled and excessive extension (as a result of the flexible loops 6 and 9 abutting the inner spinous processes) and flexion (as a result of the anchoring by serrated teeth 21*a*, 21*b*, 22*a*, and 22*b*). Thus, the implant 1 allows for a limited amount of dynamic movement between the adjacent spinous processes due to the flexibility of the loops 6 and 9 and the distance between the lower 7 and 17 and upper 8 and 18 portions respectively. The amount of movement between the adjacent spinous processes is controlled by the flexibility of the loops 6 and 9.

Figure 2:
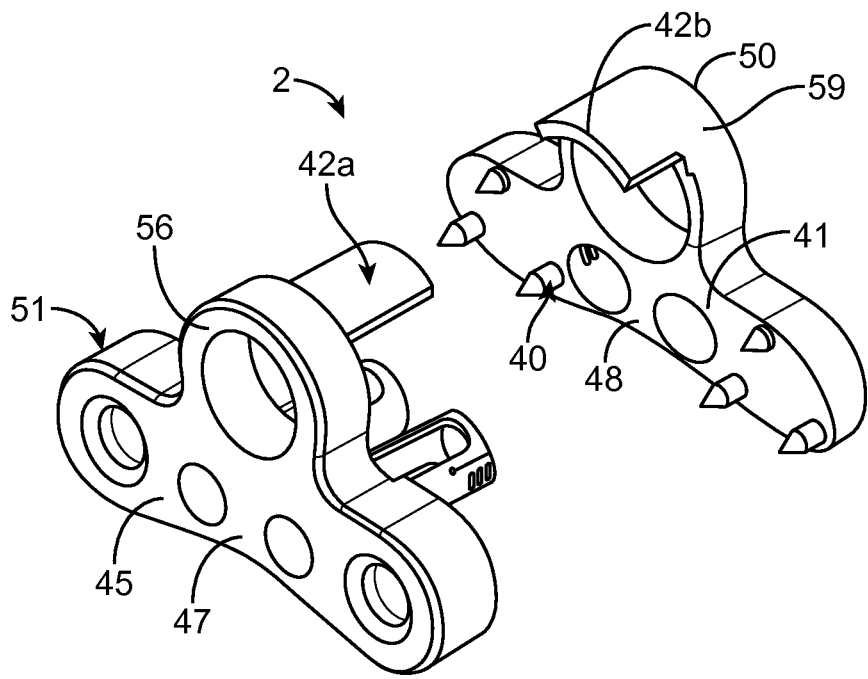
FIG. 2 is an exploded isometric view of an interspinous implant in accordance with another embodiment.

FIG. 2 shows an embodiment of a nondynamic interspinous implant 2. This implant is similar to implant 1, but rather than a disjoined pair of loops 6 and 9, it has a pair of opposing cylindrical barrel regions 56 and 59 on opposing male and female components 51 and 50 respectively. The barrel regions 56 and 59 can be semi-rigid and allow for some distortion thus allowing for some amount of controlled flexion and extension between spinous processes, or they can be rigid and not allow any distortion or flexing. Male component 51 contains a lateral plate 45 with a process fixation region 47 that allows opposite ends of the plate 45 to be secured to successive spinous processes. Likewise female component 50 has a lateral plate 41 with a process fixation region 48 that allows opposite ends of the plate 41 to be secured to the other side of the same successive spinous processes to which the fixation region 47 is secured. Each of plates 45 and 41 has transverse inwardly facing spikes 40 that can penetrate into bone. The spikes 40 can be replaced with serrated teeth such as those of implant 1. The inside surfaces of the plates 41 and 45 can be angled as shown in FIG. 2 to match the outer walls of the spinous processes. Male component 51 has a seat 42*a* that nests with counter-seat 42b of female component 50. Seat 42a is curved to match the curve of counter seat 42b and nests concentrically with counter seat 42b to form a bone graft retainer. Bone graft material is packed onto bone graft retainer, which prevents the bone graft material from migrating into the spinal canal during surgical implantation. The bone graft material aids in the fusion process between successive spinous processes. The openings of cylindrical barrel regions 56 and 59 allows for insertion of the bone graft material after implant 2 has been implanted and fixed in place between two successive spinous processes. The connection between the male and female components 51 and 50 respectively is the same as implant 1 of FIG. 1, and implant 2 is implanted in the same manner as implant 1.

Figure 3:
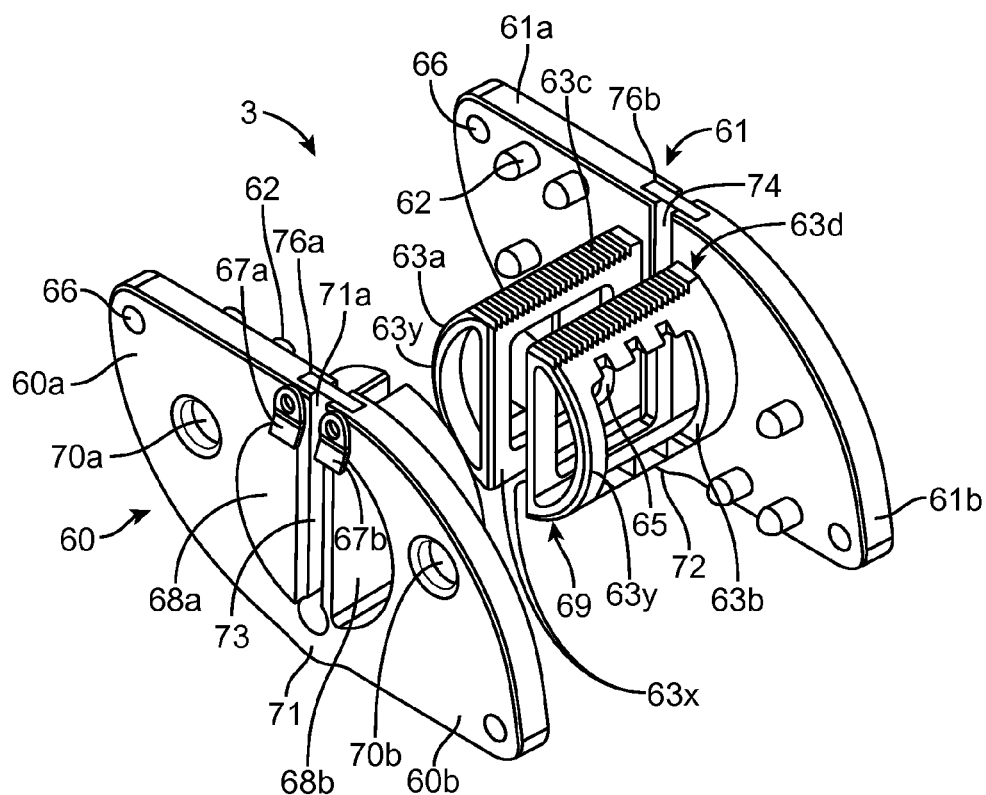
FIG. 3 is an exploded isometric view of an interspinous implant in accordance with yet another embodiment.

FIG. 3 shows another embodiment of a dynamic interspinous implant 3 made of two separate but interlocking components, male component 61 and female component 60. The two components 61 and 60 are shown in an exploded view in FIG. 3, but they are locked together when implanted as described further herein. Female component 60 has two arms projecting up and down respectively from a central flex joint 71. The first arm 60a projects in an upward or superior direction from flex joint 71, and the second arm 60b projects in a downward or inferior direction from flex joint 71. Both arms 60a and 60b are integrally formed in a unibody construction with one another and are connected to one another at flex joint 71. A gap 73 is formed between first arm 60a and second arm 60b. In its resting state when no forces are exerted on male component 61, the size of gap 73 is between about 1.0 mm and 10.0 mm, so that the gap 73 can be about 1.0 mm, 1.5 mm, 2.0 mm, 2.5 mm, 3.0 mm, 3.5 mm, 4.0 mm, 4.5 mm, 5.0 mm, 5.5 mm, 6.0 mm, 6.5 mm, 7.0 mm, 7.5 mm, 8.0 mm, 8.5 mm, 9.0 mm, 9.5 mm, 10.0 mm, or 10.5 mm. Flex joint 71 allows arms 60a and 60b to splay apart for a controlled and limited distance. This allows gap apex 71a to close entirety or to grow. The gap apex 71a can grow by no more than triple its resting distance. For example, if gap apex 71a at rest is 3.0 mm, it can spread to no more than about 9.0 mm. In another embodiment, gap apex 71a can grow by no more than between about 1.0 mm and about 10 mm, and in one embodiment, no more than by about 5.0 mm. This allows for a limited amount of controlled flexion and extension between the adjacent spinous processes that are separated by the implant 3. At maximum compression (during extension of the spinal column), there is no gap between the first and second arms 60a and 60b at gap apex 71a, i.e., the gap is closed.

Arms 60a and 60b have compression recesses 70a and 70b. Compression recesses 70a and 70b receive a compression tool that is used to squeeze male component 60 and female component 61 toward one another. Although not visible in FIG. 3, male component 61 has corresponding compression recesses on outer sides of arms 61a and 61b that receive a compression tool as well. The inner sides of arms 60a and 60b have spikes 62 that extend in a transverse direction toward male component 61 and fixedly engage with bone of the spinous process. The inner sides of arms 61a and 61b of male component 61 also has spikes 62 that extend in a transverse direction toward the female component 60. Alternatively, the inner sides of arms 60a and 60b and 61a and 61b respectively can have serrated teeth that engage the bone instead of or in addition to spikes 62. Female component 60 and male component 61 also have holes 66 on the corners of arms 60a and 60b. These holes 66 receive surgical thread or metal wire that is used to loop around spinous processes for additional stability and security.

Like female component 60, male component 61 has two arms projecting up and down respectively from a central flex joint 72. The first arm 61a projects in an upward or superior direction from flex joint 72, and the second arm 61b projects in a downward or inferior direction from flex joint 72. Both arms 61a and 61b are integrally formed in a unibody construction with one another and are connected to one another at flex joint 72. A gap 74 is formed between first arm 61a and second arm 61b. In its resting state when no forces are exerted on male component 61, the size of gap 74 is between about 1.0 mm and 10.0 mm, so that gap 74 can be about 1.0 mm, 1.5 mm, 2.0 mm, 2.5 mm, 3.0 mm, 3.5 mm, 4.0 mm, 4.5 mm, 5.0 mm, 5.5 mm, 6.0 mm, 6.5 mm, 7.0 mm, 7.5 mm, 8.0 mm, 8.5 mm, 9.0 mm, 9.5 mm, 10.0 mm, or 10.5 mm. Flex joint 72 allows arms 61a and 61b to splay apart for a controlled and limited distance. This allows the apex of gap 74 to close entirety or to grow. The apex of gap 74 can grow by no more than triple its resting distance. For example, if the apex of gap 74 at rest is 3.0 mm, it can spread to no more than 9.0 mm. In another embodiment, the apex of gap 74 can grow by no more than between 1.0 mm and 10 mm, and in one embodiment, no more than by 5.0 mm. This allows for a limited amount of controlled flexion and extension between the adjacent spinous processes that are separated by implant 3. At maximum compression (during extension of the spinal column), there is no gap between the first and second arms 61a and 61b at the apex of gap 74, i.e., the gap is closed. All of this corresponds with the flexibility of the female component 60. Thus, the properties of gap 73 and gap 74 can be the same, so that the gap distance, splaying ability and maximum splaying distance are the same for gaps 73 and 74.

Male component 61 has a bone abutment 69 that is formed by two opposing arched abutments 63a and 63b with the flat sides 63x (or bases of the arches) adjacent each other and the arched sides 63y directed away from each other. Arched superior abutment 63a extends from the inner side of arm 61a and is transverse to arm 61a and substantially perpendicular to arm 61a. Arched inferior abutment 63b extends from the inner side of arm 61b and is transverse to arm 61b and substantially perpendicular to arm 61b. Flat sides or bases 63x of each of arched abutments 63a and 63b are parallel to gap 74 and face each other. Where the arch 63y and base 63x of each of arched abutments 63a and 63b meet at the top is a column of zip-lock teeth 63c and 63d respectively. Each of columns 63c and 63d of zip-lock teeth is shown as extending the entire length of the base of each arched abutment 63a and 63b respectively. However, the columns may not extend the entire length of the arched abutments 63a and 63b. For example, in one embodiment, the columns of teeth 63c and 63d may start at the distal end of the arched abutments 63a and 63b and extend only part of the way (e.g., ¾ of the way, ⅔ of the way, ½ of the way, ⅓ of the way, or ¼ of the way), toward the arms 61a and 61b respectively, and not extend all the way to the arms 61a and 61b. In one embodiment, the arched abutments 63a and 63b each has only one set of columns of zip-lock teeth as shown in FIG. 3. In another embodiment (not shown), where the arch 63y and base 63x of each of arched abutments 63a and 63b meet at the bottom is another column of zip-lock teeth on each of the arched abutments 63a and 63b that are on the opposite side of the abutments from columns 63c and 63d.

Each of the arched abutments 63a and 63b slides into a correspondingly shaped opening 68a and 68b respectively in female component 60. Arched superior abutment 63a slides into opening 68a that forms an arched tunnel that receives the arched abutment 63a. Arched inferior abutment 63b slides into opening 68b that forms an arched tunnel that receives the arched abutment 63b. The distal ends of each of arched abutments 63a and 63b slide into their corresponding openings 68a and 68b on the inner side of female component 60, and they slide through the openings and out of the openings 68a and 68b respectively on the outer side of female component 60. On the other side of the openings 68a and 68b are latches 67a and 67b respectively. The latches are biased outward away from the outer side of the female component 60. As the abutments 63a and 63b slide through openings 68a and 68b, the columns of teeth 63c and 63d slide past latches 67a and 67b respectively. The teeth are angled backwards so that the latches slide over the angled top sides of the teeth. However, latches 67 and 67b will catch against the back sides of the teeth and prevent the abutments 63a and 63b from sliding back out of the openings 68a and 68b. In order to release male component 61 from female component 60, latches 67a and 67b respectively can be rotated around a screw so that latches 67a and 67b are rotated away from the teeth of the columns 63c and 63d. Once latches 67a and 67b are rotated away from the teeth and no longer catch against the back side of the teeth, the male component 61 can be pulled back out of the female component 60. This zip-lock mechanism allows for a secure coupling between the male 61 and female 60 components. Another benefit is that a set screw is not required, nor is there a requirement for additional tools to secure the two components to one another. Simply sliding the male component 61 into the female component 60 results in a lock between the two components without additional handling.

The implant 3 is dynamic, but it has a feature that can be used to make it non-dynamic. Each of abutments 63a and 63b have one or more notches 65 (3 shown in FIG. 3) on their arch side 63y. Metal rings can be fitted around the abutments 63a and 63b that fit into the notches 65. The rings prevent the abutments 63a and 63b from spreading apart and away from each other. The abutments 63a and 63b are attached (or formed integrally) to arms 61a and 61b respectively. As a result of the abutments not being able to spread away from each other, arms 61a and 61b are prevented from splaying away from each other and allowing gap 74 to widen. Also, when the distal ends of the abutments are in the openings 68a and 68b, arms 60a and 60b are prevented from splaying. This is because there is a tight fit between the outer surface of abutments 63a and 63b and the inner surface of their respective openings 68a and 68b, and when the abutments are prevented from splaying or spreading, this prevents the arms 60a and 60b from splaying, effectively locking the gap 71a at a fixed maximum distance. The rings do not prevent gaps 71a and 74 from closing, thus the implant remains partly dynamic in that it allows for some extension between the spinous processes. In other words, when the spinal column undergoes extension, the spinous processes are squeezed towards each other and they squeeze the abutments 63a and 63b toward each other as a result of the superior process being forced downward against abutment 63a while abutment 63b is then forced against the inferior spinous process, thus causing the abutments 63a and 63b to be forced towards each other closing gaps 73 and 74. In another embodiment, in which the implant can be made completely non-dynamic, i.e., preventing both flexion and compression, rigid connector 76a on female component 60 can be used to lock the two arms 60a and 60b with respect to one another and thus prevent any movement between the two arms 60a and 60b. This will lock the gap 71a at a fixed distance. Likewise, rigid connector 76b on male component 61 can be used to lock the two arms 61a and 61b with respect to one another and thus prevent any movement between the two arms 61a and 61b. This will lock gap 74 at a fixed distance. Once connector 76a is connected to both the arms 60a and 60b across gap 71a, it forms a rigid connection lock between arms 60a and 60b. Thus, arms 60a and 60b can no longer move with respect to one another, and gap 73 between them becomes fixed. Likewise, once connector 76b is connected to both arms 61a and 61b across gap 74, it forms a rigid connection lock between arms 61a and 61b. Thus, arms 61a and 61b can no longer move with respect to one another, and gap 74 between them becomes fixed. In this way, the arms cannot splay apart or come together. Thus, implant 3 becomes non-dynamic and prevents flexion and extension between adjacent spinous processes. The abutments 63a and 63b prevent extension and spikes 62 prevent flexion.

In one method of implantation, the assembled interspinous implant 3 can be inserted between two spinous processes of adjacent vertebrae in an anterior to posterior direction after severing spinous ligaments to remove them from the path of implantation. In another method of implantation, no spinous ligaments are severed and the male and female components 61 and 60 are separated and can each individually be inserted from opposing lateral directions toward each other anterior to the undisturbed spinous ligaments. Once the implant 3 is inserted between successive spinous processes, the male component 61 and female component 60 are brought toward each other so that the abutments 63a and 63b slide into openings 68a and 68b respectively. The two components are squeezed toward each other until the inner sides of the arms of each component come into contact with the outer side of the adjacent spinous processes. Arms 61a and 60a come into contact with the superior spinous process while arms 61b and 60b come into contact with the spinous process just inferior to the spinous process contacted by arms 61a and 60a. The two components 60 and 61 are further squeezed together as the teeth of the zip-lock columns 63c and 63d engage with the latches 67a and 67b, and the latches 67a and 67b catch against the teeth and lock the male component 61 to the female component 60 and prevent the two from coming apart. The two components (male 61 and female 60) are further squeezed together until spikes 62 penetrate the bone on the outer sides of the successive spinous processes and form a tight grip on the two successive spinous processes. When that happens, the implant is securely in place with no need for further screwing. If fusion is the required result, then the arms can be locked together as described above, thus preventing any movement between the successive spinous processes and aiding in fusion between the two. If some movement is desired, then the arms are not locked against one another and the implant 3 allows for some dynamic movement between the spinous processes.

Figure 4:
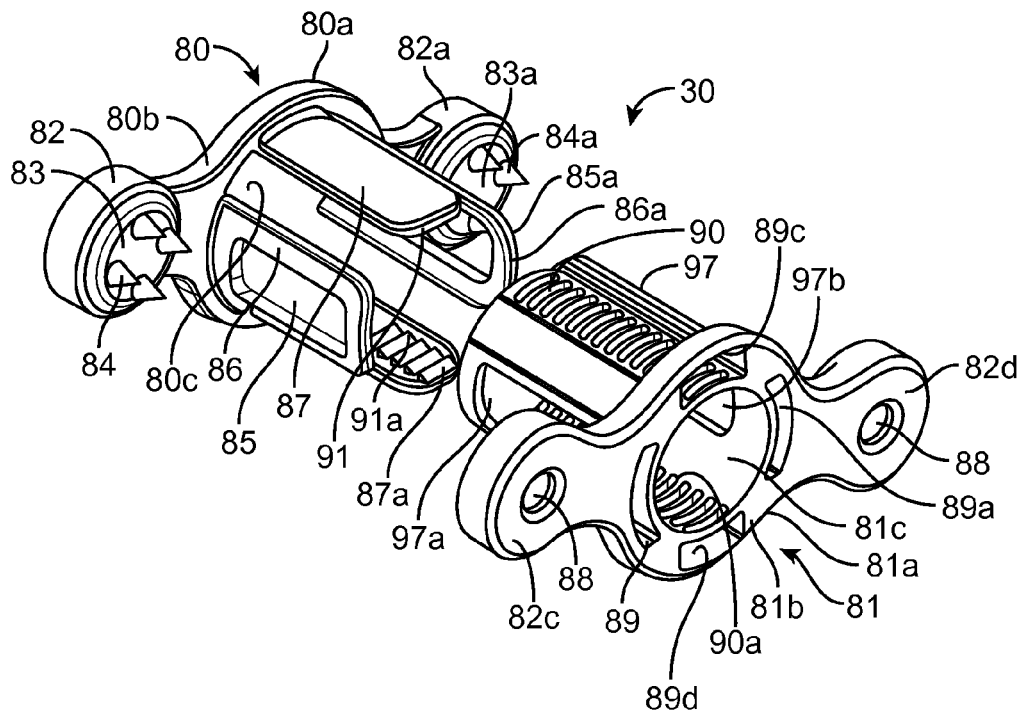
FIG. 4 is an exploded isometric view of an interspinous implant in accordance with yet another embodiment.

FIG. 4 is an exploded perspective view of another embodiment of an interspinous fusion implant ("ISP") 30. Like implant 2, ISP 30 is non-dynamic. It is made of two interconnecting components, a first implant component 80 and a second implant component 81. Each of implant components 80 and 81 include subcomponents that will be described further.

Implant component 80 includes a lateral bone spacer 80a. Lateral bone spacer 80a has a center ring 80b. Center ring 80b forms a round opening 80c through which various substances, such as bone grafts or natural or synthetic bone growth stimulating substances, such as synthetic or natural bone matrix, may be passed through opening 80c. Extending laterally in one direction from center ring 80b is superior bone anchor housing 82.

Extending laterally in the exact opposite direction from center ring 80b is inferior bone anchor housing 82a. Both superior and inferior bone anchor housings 82 and 82a can be circular in shape for optimum anchoring capacity to the spinous process. In one embodiment, the superior and inferior bone anchor housings 82 and 82a are the same shape and size.

In other embodiments, they are different shapes and/or sizes. In one embodiment, a straight line runs through the center of each of housings 82, 82a and center ring 80b, i.e., they are at an angle of 180° from one another as shown in FIG. 4. The distance between the ends of superior and inferior bone anchor housings 82 and 82a can be between about 30 mm and about 50 mm. In one embodiment, it is between about 35 mm and about 40 mm. In other embodiments, it is about 30 mm, 35 mm, 40 mm, 45 mm or 50 mm.

Within each of bone anchor housings 82 and 82a are self-aligning bone anchor assemblies 83 and 83a respectively. Each of bone anchoring assemblies 83 and 83a contain one or more (four as shown in FIG. 4) spikes 84 and 84a respectively that can penetrate bone. Spikes 84 and 84a protrude transversely in an inward direction from bone anchoring assemblies 83 and 83a. Spikes 84 and 84a are designed to penetrate the bone of the spinous process. While spikes 84 penetrate one spinous process, spikes 84a penetrate the next spinous process inferior to the one being penetrated by spikes 84. In addition, superior and inferior anchor housings 82 and 82a may be made of a unibody construction with center ring 80b, or alternatively, they may be secured to arms projecting from center ring 80b by pins or other means that permit superior and inferior anchor housings 82 and 82a to freely pivot at an angle relative to center ring 80b.

Projecting transversely from the inner side of lateral bone spacer 80a and at a substantially 90° angle from lateral bone spacer 80a are two opposing zip lock flanges 87 and 87a, and two opposing bone abutments 86 and 86a. Alternatively, flanges 87 and 87a can be slightly biased inward toward each other for the purpose of forming a tight grip on barrel 97. A longitudinal axis extends from the center of center ring 80b to the distal ends of zip lock flanges 87 and 87a and bone abutments 86 and 86a. Zip lock flanges 87 and 87a are slightly curved along their width forming the same arc as the circular center ring 80b from which they extend transversely. Zip lock flanges 87 and 87a are opposite each other and face each other as shown in FIG. 4. At the distal end of each of zip lock flanges 87 and 87a are one or more zip lock locking teeth 91 and 91a respectively that protrude from the inward facing surfaces of zip lock flanges 87 and 87a respectively. FIG. 4 shows that flanges 87 and 87a have five zip lock teeth, but it can be fewer or more than that number of teeth, such as 6, 7, 8, 9, 10 or more teeth. Each of zip lock teeth 91 and 91a form a top angled sliding face and a back locking ridge as shown in FIG. 4. The sliding face is angled to allow the teeth to slide forward and mate with the zip lock recesses or holes in the second implant component 81. The back locking ridge of teeth 91 and 91a can form a substantially 90° angle with the zip lock flanges 87 and 87a or they can be angled toward the center ring 80b thus forming an acute angle between the back locking ridge and zip lock flanges 87 and 87a. If the angle is acute, then teeth 91 and 91a will be taller (i.e., they will extend further from their respective zip lock flange 87 and 87a) than when the angle is a substantially 90° angle for reasons that will be explained further below. The longer teeth will protrude through recesses 90 and 90a at an angle thus creating a force that pulls second implant component 81 toward zip lock flanges 87 and 87a and prevents splaying of flanges 87 and 87a away from implant component 81. However, when the angle is substantially 90° and the walls forming the holes or recesses 90 and 90a are at 90°, then there is greater surface area contact between the back ridge of teeth 91 and 91a and the walls of recesses 90 and 90a, which increases the forces between teeth 91 and 91a and their respectively mated recesses 90 and 90a. The 90° configuration also reduces the risk of teeth breaking since the pressure on the back ridge is spread out across the entire surface area of the ridge rather than on just the narrow strip that makes contact with the edges of recesses 90 and 90a. Teeth 91 and 91a lock first and second components 80 and 81 longitudinally, radially, and transversely with respect to one another due to the forces between teeth 91 and 91a and recesses 90 and 90a into which they slide. The outward facing surfaces of zip locking flanges 87 and 87a are substantially smooth.

Bone abutments 86 and 86a face each other and extend transversely from center ring 80b. As shown in FIG. 4, they are both slightly rounded along their width thus forming the same arc as circular center ring 80b from which they extend transversely. Each of bone abutments 86 and 86a has a fusion window 85 and 85a respectively. Fusion windows 85 and 85a allow fusion between adjacent spinous processes through the barrel formed by the connection between the first and second implant components 80 and 81. The outer facing surface of bone abutments 86 and 86a may be smooth. Alternatively, they may be roughened to form more friction between bone abutments 86 and 86a and the spinous processes which they respectively abut. Increased friction will minimize any movement between the spinous processes and ISP 30 once ISP 30 is implanted between adjacent spinous processes.

Second implant component 81 mates with first implant component 80. Second implant component 81 has a lateral bone anchor 81a that faces and mirrors lateral bone spacer 80a. Lateral bone anchor 81a has a main function that is different than that of lateral bone spacer 80a. Whereas lateral bone spacer 80 has abutments 86 and 86a extending transversely to abut adjacent spinous processes and to keep the adjacent spinous processes separated from one another at a predetermined distance corresponding with the distance between the two bone abutments 86 and 86a, the primary purpose of lateral bone anchor 81 is not to have abutments extending from it, but to instead have a connecting barrel 97 extending transversely from it, which allows lateral bone spacer 80a and lateral bone anchor 81a to move toward or away from one another and to form a lock once the proper distance for anchoring to the spinous processes is determined.

Like lateral bone spacer 80a, lateral bone anchor 81a has a center ring 81b. Center ring 81b forms a round opening 81c through which various substances, such as natural or synthetic bone grafts or bone growth stimulating substances such as natural or synthetic bone matrix, may be passed through center ring 81b. Extending laterally in one direction from center ring 81b is superior bone anchor housing 82c. Extending laterally in the exact opposite direction from center ring 81b is inferior bone anchor housing 82d. Both superior and inferior bone anchor housings 82c and 82d can be circular in shape for optimum anchoring capacity to the spinous process. In one embodiment, superior and inferior bone anchor housings 82c and 82d are the same shape and size. In other embodiments, they are different shapes and/or sizes. In one embodiment, a straight line runs through the center of each of housings 82c, 82d and center ring 81b, i.e., they are at an angle of 180° from one another as shown in FIG. 4. The distance between the ends of superior and inferior bone anchor housings 82c and 82d can be between about 30 mm and about 50 mm. In one embodiment, it is between about 35 mm and about 40 mm. In other embodiments, it is about 30 mm, 35 mm, 40 mm, 45 mm or 50 mm. In any case, the distance between the ends of bone anchor housings 82c and 82d will be the same as the distance between the ends of bone anchor housings 82 and 82a.

Within each of housings 82c and 82d are self-aligning bone anchor assemblies (reference numbers not shown). Each of said bone anchoring assemblies contain one or more (four in one embodiment) spikes that can penetrate bone. The spikes are the same as spikes 84 and 84*a*, and they protrude transversely from the inner side of bone anchoring assemblies 82*c* and 82*d*. The spikes are designed to penetrate the bone of the spinous process. While spikes extending from bone anchor housing 82*c* penetrate one spinous process, spikes extending from bone anchor housing 82*d* penetrate the next spinous process inferior to the one being penetrated by spikes extending from bone anchor housing 82*c*. In addition, superior and inferior anchor housings 82*c* and 82*d* may be made of a unibody construction with center ring 81*b*, or alternatively, they may be secured to arms projecting from center ring 81*b* by pins or other means that permit superior and inferior anchor housings 82*c* and 82*d* to freely pivot at an angle relative to center ring 81*b*. The outer sides of bone anchoring assemblies 82, 82*a*, 82*c* and 82*d* have indentations 88 that receive a compression tool that is used to force the components 80 and 81 toward each other and form a zip-locked engagement as the compression tool forces flanges 87 and 87*a* to slide over barrel 97.

Center ring 81*b* has holes 89 and 89*a* that are arcuate and are shaped and sized to receive the distal ends of the bone abutments 86 and 86*a* respectively. Holes 89 and 89*a* are opposite each other on the center ring 81*b*. When the bone abutments 86 and 86*a* mate respectively with holes 89 and 89*a*, first and second components 80 and 81 are prevented from spinning relative to one another, and they become locked radially in place with respect to one another (see FIG. 5). Center ring 81*b* also has holes 89*c* and 89*d* that are arcuate and are shaped and sized to receive the distal ends of zip lock flanges 87 and 87*a* respectively (see FIG. 5).

Projecting transversely from the inner side of lateral bone anchor 81*a* and at a substantially 90° angle from lateral bone anchor 81*a* is a barrel 97. Barrel 97 can have a diameter of between about 5.0 mm and about 25 mm. In various embodiments, it has a diameter of about 5.0 mm, 6.0 mm, 7.0 mm, 8.0 mm, 9.0 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm or 25 mm. The length of barrel 97 can be between about 15 mm and about 30 mm. In various embodiments, it has a length of about 15 mm, 16 mm, 17 mm, 18 mm, 19 mm, 20 mm, 21 mm, 22 mm, 23 mm, 24 mm, 25 mm, 26 mm, 27 mm, 28 mm, 29 mm or 30 mm. Barrel 97 contains two columns of zip lock recesses 90 and 90*a*. Zip lock recesses 90 are opposite zip lock recesses 90*a* on the barrel 97. The column of zip lock recesses 90 is aligned with hole 89*c*, and the column of zip lock recesses 90*a* is aligned with hole 89*d*. Zip lock recesses 90 receive and mate with teeth 91 of zip lock flange 87, and zip lock recesses 90*a* receive and mate with teeth 91*a* of zip lock flange 87*a*. In on embodiment, as shown in FIG. 4, zip lock recesses 90 and 90*a* are elongated holes or slits that are shaped to receive teeth 91 and 91*a* respectively. In another embodiment (not shown in the figures) zip lock recesses 90 and 90*a* are formed by protruding teeth that extend radially outward from the barrel 97. Such teeth can be angled or sloped in the opposite direction of teeth 91 and 91*a* so that teeth 91 and 91*a* will slide over teeth 90 and 90*a* respectively when components 80 and 81 are forced into engagement with each other. When teeth 91 and 91*a* engage with teeth 90 and 90*a* respectively component 80 cannot be pulled apart from component 81, because the vertical back side of teeth 91 and 91*a* will catch against the vertical front side of teeth 90 and 90*a* respectively. In yet another embodiment, zip-locks recesses are formed by straight vertical protuberances over which teeth 91 and 91*a* slide. When teeth 91 and 91*a* engage with teeth protuberances 90 and 90*a* respectively component 80 cannot be pulled apart from component 81, because the vertical back side of teeth 91 and 91*a* will catch against the vertical protuberances 90 and 90*a* respectively. Barrel 97 also has windows 97*a* and 97*b* that are opposite one another on barrel 97. Windows 97*a* and 97*b* are the same size and shape as windows 85 and 85*a* and align with windows 85 and 85*a* respectively when components 80 and 81 are mated to one another.

First and second components 80 and 81 mate with one another in the following manner. As the two are brought toward one another, zip lock flanges 87 and 87*a* glide over the columns of zip lock recesses 90 and 90*a* respectively of barrel 97. As flanges 87 and 87*a* glide over barrel 97, bone abutments 86 and 86*a* glide over barrel 97 as well, and windows 85 and 85*a* become aligned respectively with windows 97*a* and 97*b* of barrel 97. Barrel 97 thus becomes nested within bone abutments 86 and 86*a* and flanges 87 and 87*a* of first component 80, such that barrel 97 becomes radially nested within first component 80 (see FIG. 5). Once windows 85 and 85*a* are aligned with windows 97*a* and 97*b* respectively, a barrel is formed by the mating of component 80 and 81 with opposing windows (85 and 97*a* form one window while 85*a* and 97*b* form another) through which bone can grow, such that bone from one spinous process can eventually fuse with bone from the adjacent spinous process through the windows. In addition, bone growth stimulating materials, such as natural or synthetic bone matrix or bone graft material, can be inserted through either of openings 80*c* or 81*c* into the barrel to help stimulate the growth of bone between the adjacent spinous processes.

Figure 5:
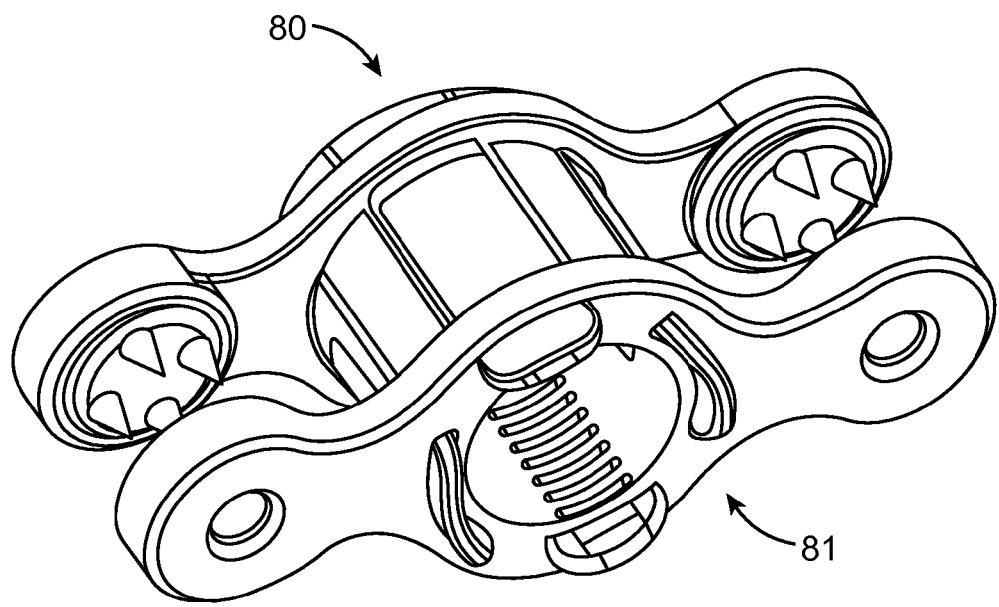
FIG. 5 is an isometric view of the interspinous implant depicted in FIG. 4 in its assembled state.

When first and second components 80 and 81 are locked with one another through the mating of teeth 91 and 91*a* with zip lock recesses 90 and 90*a* respectively, anchor housings 82 and 82*c* are aligned opposite with one another along a single longitudinal axis, and anchor housings 82*a* and 82*d* are aligned opposite with one another along a single longitudinal axis (see FIG. 5).

When components 80 and 81 are mated as described above, they cannot be disengaged from one another without the use of a splaying tool that splays the zip-lock flanges 87 and 87*a* away from barrel 97. Thus, the two components 80 and 81 are reversibly locked together, but they cannot be disengaged or unlocked from one another except with the use of a splaying tool. Thus, component 81 can slide into component 80 and become reversibly locked to component 80 without any additional tools, but the two components cannot be separated from one another once they are engaged without a release tool that splays zip-lock flanges 87 and 87*a* radially apart from barrel 97. This results in ISP 30 being a device that can be locked to the spinous processes without a set screw or screw drivers or the need for any additional locking tools that require adjustment of screws. Components 80 and 81 need only be pushed or forced together and they will form a tight lock to one another that is not prone to failure and is only reversible with a splaying tool. This is a significant improvement over older implants that require additional tooling to be secured in place between spinous processes. The columns of multiple or a series of teeth 91 and 91*a* mating with multiple or a series of recesses 90 and 90*a* respectively prohibits the migration of component 81 away from component 80 once the two components are engaged to one another through the described zip-locking mechanism, and this minimizes the risk of long-term mechanical failure of ISP 30 once it has been implanted. These same features, benefits, and improvements are also equally applicable to ISP 200, ISP 285, and ISP 300 described later herein, because they both have the same zip-lock mechanism as ISP 30.

Figure 6:
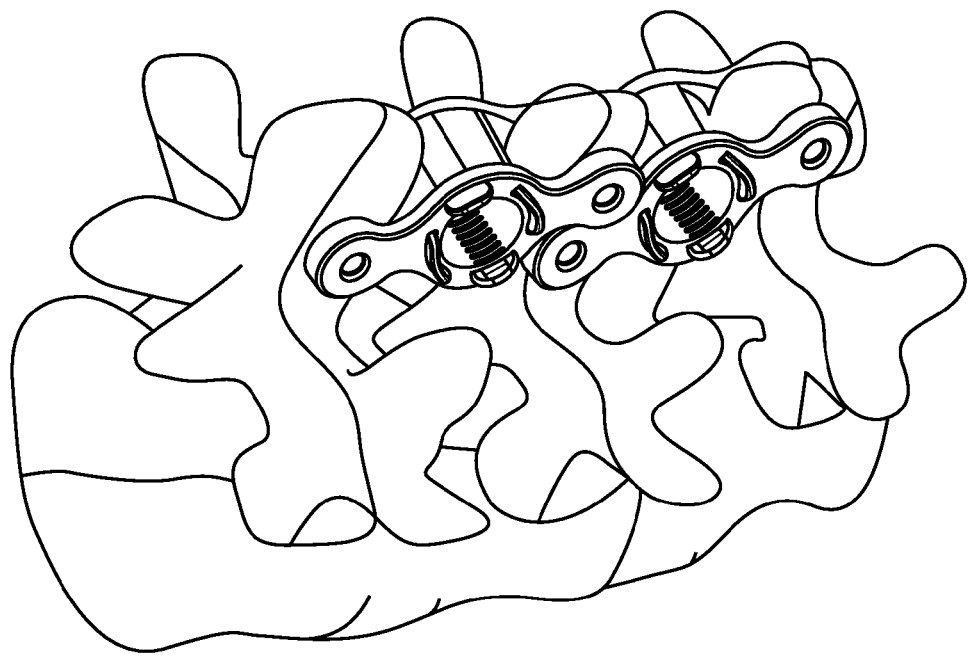
FIG. 6 is a three dimensional illustration of two of the interspinous implants depicted in FIG. 4 implanted in a successively stacked configuration.

First and second components 80 and 81 mate with one another to form a single ISP unit that not only separates two adjacent spinous processes from one another at a predetermined distance, but keeps them locked with respect to one another as a result of the penetration of the spinous processes by the anchoring spikes (described above). The bone abutments 86 and 86*a* thus prevent extension between adjacent spinous processes, while the anchors prevent flexion between two adjacent spinous processes (see FIG. 6).

In one method of implantation, the assembled ISP 30 can be inserted between two spinous processes of adjacent vertebrae in an anterior to posterior direction after severing spinous ligaments to remove them from the path of implantation. In another method of implantation, no spinous ligaments are severed and the first and second components 80 and 81 are separated and can each individually be inserted from opposing lateral directions toward each other anterior to the undisturbed spinous ligaments. In any case, the ISP 30 is inserted between two spinous processes of adjacent vertebrae, and multiple ISP units can be stacked one after another (see FIG. 6). First and second components 80 and 81 are squeezed or pushed toward one another until the spikes on opposing anchor housings 82 and 82*c* penetrate the outer sides of the superior spinous process while the spikes on anchoring housings 82*a* and 82*d* penetrate the outer sides of the adjacent and inferior spinous process. With the penetration of the spikes the ISP 30 prohibits both extension (as a result of bone abutments 86 and 86*a* abutting the inner spinous process) and flexion (as a result of the anchoring by the spikes).

The locking mechanism described with respect to FIG. 4 is the mating of a series of successive teeth 91 and 91*a* with a series of successive recesses 90 and 90*a* respectively. This locking mechanism poses a significant advantage over previous locking mechanisms that use set screws, nuts or bolts. The use of a series of successive teeth (i.e., two or more teeth, e.g., two, three, four, five, six, seven, eight, nine, ten or more teeth) creates forces that are significantly greater than can be achieved using a set screw, nut or bolt. Moreover set screws can loosen and come undone with time allowing the two parts of a spinal implant to slide apart from each other. The use of a series of successive zip locking teeth, such as in FIG. 4, prevents this problem. Moreover, disengagement of the described first and second components 80 and 81 from one another requires a two-step process: pulling the flanges 87 and 87*a* apart from one another (a radial spreading force) while simultaneously pulling components 80 and 81 longitudinally away from one another (a longitudinal pushing or pulling force). The likelihood of both forces occurring at the same time inadvertently or through failure of the device over time are much lower than devices that use set screws, where the screw can become undone over time and then subsequent movement of the two parts away from each other can happen at a later time thus causing a failure of the device in situ. This type of locking mechanism is also a significant improvement over a simple ratchet, because a ratchet does not create the firm grip and increased forces created by the engagement of a series of successive teeth with a series of successive recesses.

ISP 30 can be packaged as part of a kit that comes with an implantation tool that controls the insertion of ISP 30 between spinous processes and a removal tool that is designed to splay the flanges 87 and 87*a* away from barrel 97 so that the two components 80 and 81 can be separated from one another. The implantation tool can be a compression tool that engages the indentations 88 on the opposing arms 82 and 82*a* on the one hand and 82*c* and 82*d* on the other hand, and squeezes the two components 80 and 81 together forcing the flanges 87 and 87*a* to advance forward over the zip-lock recess columns 90 and 90*a* respectively and toward and through openings 89*c* and 89*d* respectively. The kit can also include synthetic or natural bone matrix that can be used with ISP 30 to promote fusion between successive vertebrae. The bone matrix can be packed in the barrel 97 promoting bone growth between a superior vertebra and an inferior vertebra through windows 85, 85*a*, 97*a*, and 97*b*. ISP connecting rods and couplers 500 can also be included in the kit. ISP 200, 285 and 300 can also be packaged as part of a kit with the same tools and materials described here with respect to ISP 30. Such kits can also come with instructions for use. The instructions for use can include the following steps, which can be part of a method of implanting ISP 30 (also ISP 200, 285 and 300):

i. Remove ISP 30 (or 200, 285 or 300) from packaging ii. Manually align the zip-lock flanges with zip-lock recess columns respectively.

iii. Manually guide zip-lock flanges over zip-lock recess columns of the barrel until at least one of the teeth of each of the zip-lock flanges respectively engages at least one of the recesses of the zip-lock recess columns respectively.

iv. Pack the barrel (this refers to barrel 97) with bone growth matrix (this step can be performed after ISP is implanted as well).

v. Implant the assembled ISP 30 (or 200, 285 or 300) by guiding the zip-locked section between adjacent spinous processes while the arms of the one component are aligned with the outer sides of the two adjacent spinous processes and the other arms of the other component are aligned with the opposite outer sides of the same two adjacent spinous processes.

vi. Adjust the angle of the ISP 30 (or 200, 285 or 300) so that it is implanted in the orientation desired. The following orientations are suggested:

1. The superior end of ISP is anterior to the inferior end of ISP, such that the superior end of ISP is adjacent the lamina of the superior spinous process while the inferior end of ISP is adjacent the posterior end of the inferior spinous process (see FIG. 6 as an example of this).

2. The superior end of ISP is posterior to the inferior end of ISP, such that the superior end of ISP is adjacent the posterior end of the superior spinous process while the inferior end of ISP is adjacent the lamina of the inferior spinous process (this is the opposite of the configuration depicted in FIG. 6).

vii. Engage the implantation tool to the indentations on the outer sides of the arms. Cause the implantation tool to squeeze the two components toward each other forcing the flanges to advance forward over the zip-lock recess columns and toward and through openings at the opposite ends (180° apart) of the barrel that receive the ends of the flanges.

viii. Cease causing the implantation tool to squeeze the two components together once the spikes on the arms of the two components have engaged the bone on opposite sides of the adjacent spinous processes and have burrowed into the bone.

ix. Check to make sure that the ISP is firmly anchored to the successive spinous processes.

x. Add additional ISPs to form a stack of successive ISPs anchored to successive spinous processes in the same manner described above.

1. If additional ISPs are implanted, they may be anchored together using the rods provided here connected to the outer sides of the arms using couplers (this feature is described in more detail below).

xi. To remove an ISP 30 (or 200, 285 or 300) use the removal tool to splay flanges on the one component away from the barrel of the other component thus disengaging teeth on the flanges from the recesses on the barrel, and pull the two components away from each other until they are disengaged from one another.

Figure 7:
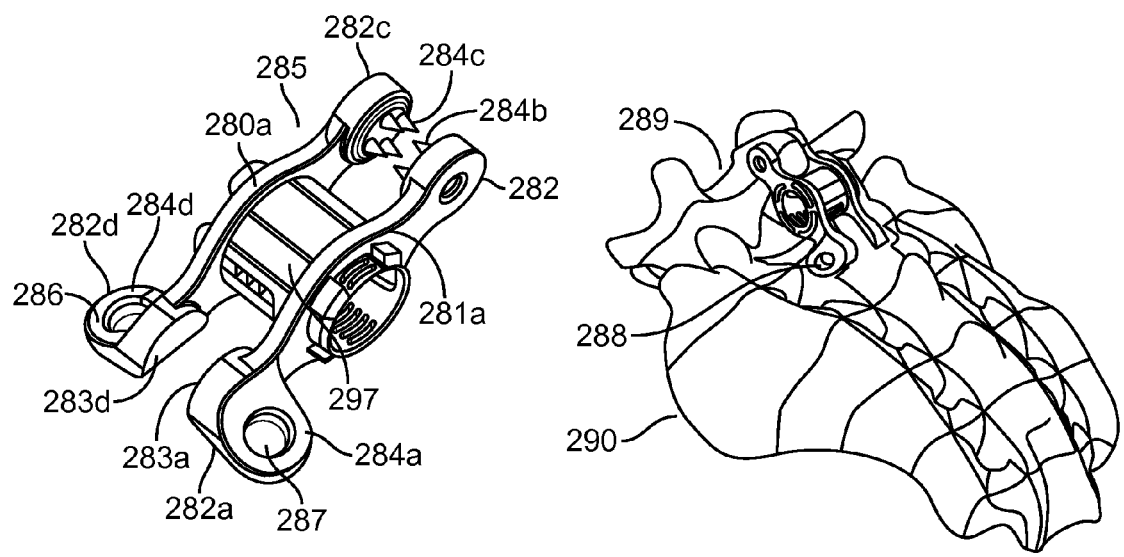
FIG. 7 is an isometric view of an interspinous implant in accordance with another embodiment and a three-dimensional illustration of said implant as it is implanted in the lower vertebral column adjacent the sacrum.

In another example, FIG. 7 depicts ISP 285, which is similar to ISP 30, except that it is designed to be used in the sacral region 290 of the vertebral column, between the last spinous process 289, which projects posteriorly from the L5 vertebral body, and the sacrum. The components of ISP 285 are the same as those of ISP 30, except that the inferior bone anchor housings 282a and 282d of ISP 285 are different from inferior bone housings 82a and 82d of ISP 30. Anchor housing 282a forms a flared wing 284a with a hole 287, and anchor housing 282d forms a flared wing 284d with a hole 286. Hole 287 and hole 286 each receives a set screw 288, that anchors the flared wings 284a and 284d respectively to the sacrum. Thus, the inferior bone anchor housings 282a and 282d of ISP 285 are anchored to the sacrum using set screws rather than spikes. In contrast, like ISP 30, superior bone housings 282c and 282 of ISP 285 use spikes 284c and 284b respectively to anchor the superior housings 282c and 282 to the spinous process of the L5 vertebral body. ISP 285 can be seen in its implanted form in FIG. 7 to illustrate the written description set forth above.

Inferior housings 282a and 282d include sacral abutments 283a and 283d from which the flared wings 284a and 284d project laterally outwardly. Abutments 283a and 283d face each other when ISP is in its assembled state. Abutments 283a and 283d can be parallel to one another in one embodiment. In another embodiment, abutments 283a and 283d are not parallel with one another, and instead they each form a slope that matches the contour of the sacrum, such that the top edges of each of abutments 283a and 283d are nearer one another than their bottom edges. Relative to a plane that runs perpendicular to barrel 297 and parallel with rings 280a and 281a, abutments 283a and 283d could form an angle of between about 0 degrees and about 45 degrees, i.e., that angle can be about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 degrees. Flared wings 284a and 284d project outwardly from the inferior housings 282a and 282d. Relative to a plane that runs perpendicular to barrel 297 and parallel with rings 280a and 281a, flared wings 284a and 284d could form an angle of between about 90 degrees and about 150 degrees, i.e., that angle can be about 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 degrees.

Figure 11:
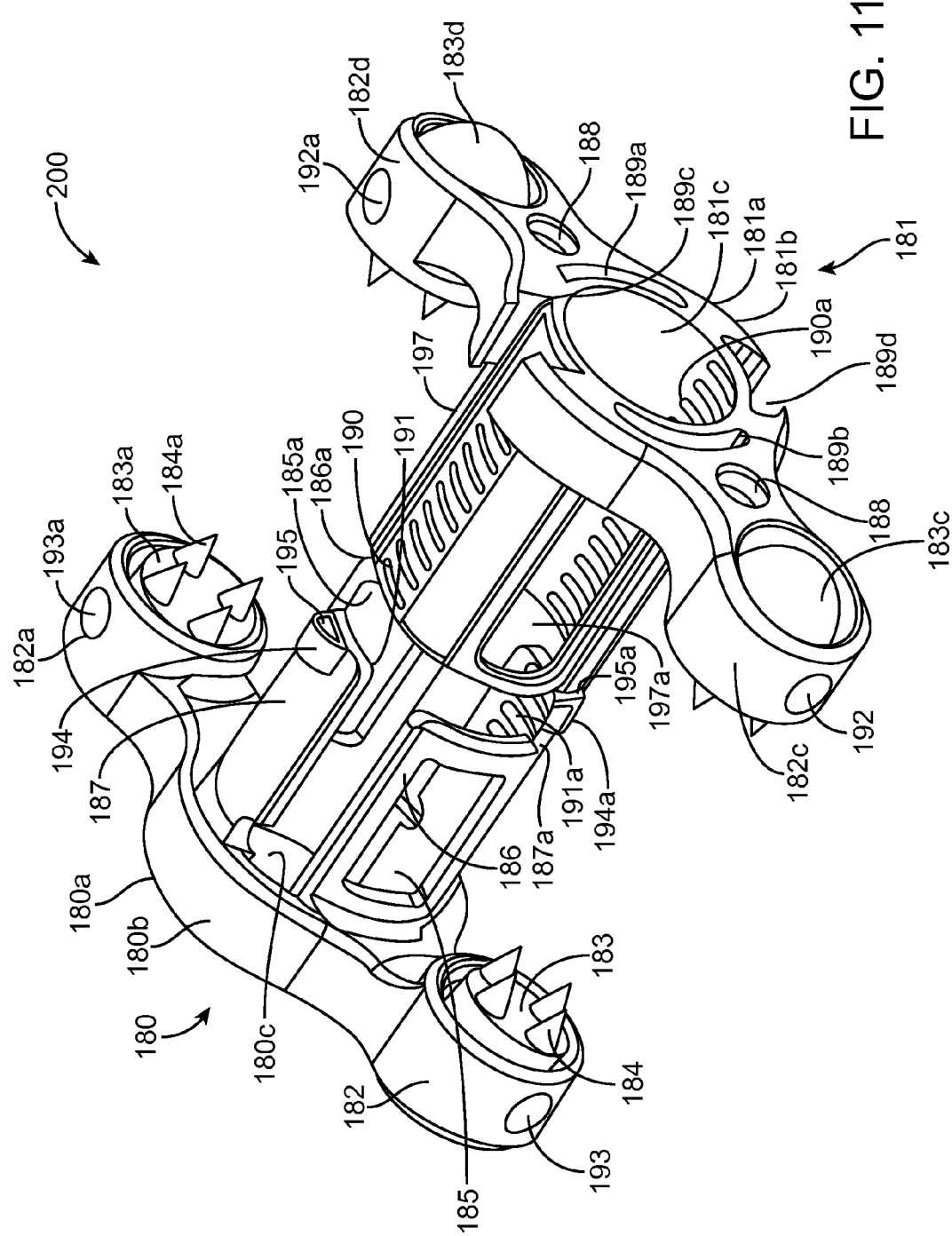
FIG. 11 is an exploded isometric view of an interspinous implant in accordance with another embodiment.
Figure 12A:
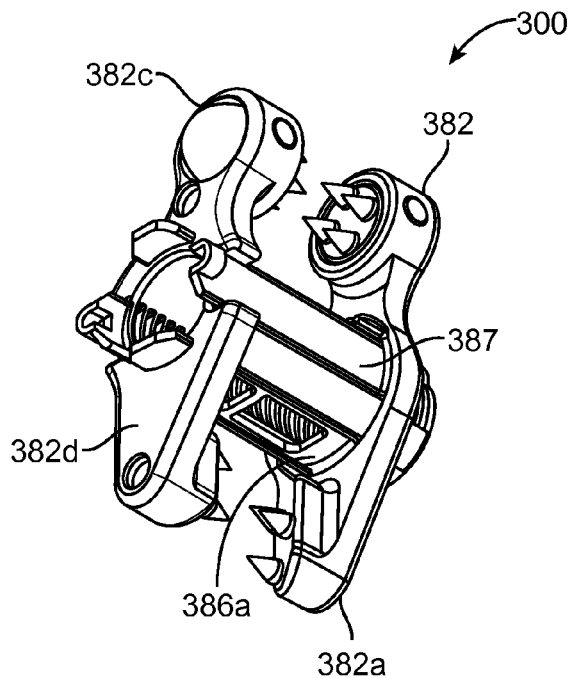
FIGS. 12a-12f are various views of an interspinous implant in accordance with another embodiment.
Figure 12B:
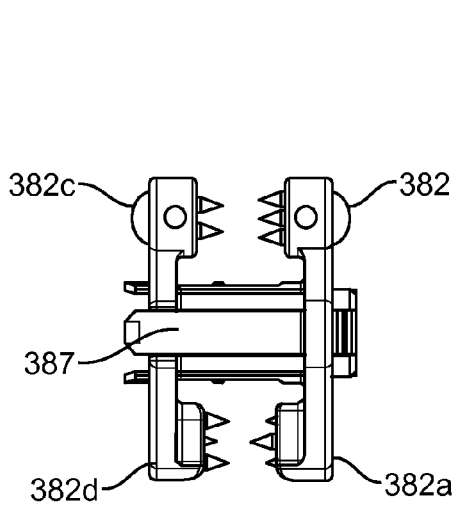
Figure 12C:
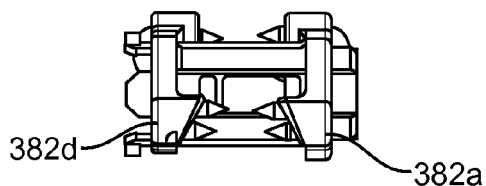
Figure 12D:
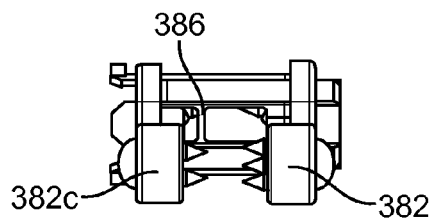
Figure 12E:
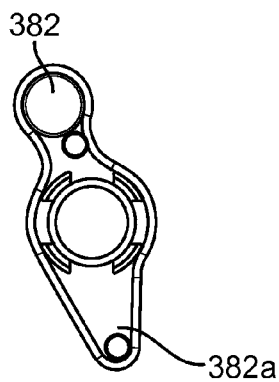
Figure 12F:
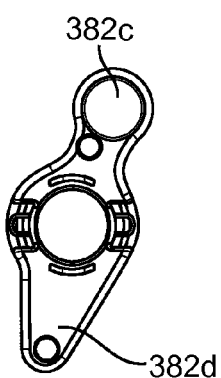

In another example, FIG. 11 is an exploded perspective view of another embodiment of an interspinous fusion implant ("ISP") 200. A first component 180 and second component 181 are fitted together and lock together to form ISP 200 in the same manner as ISP 30 of FIG. 4. ISP 200 is similar to ISP 30 but with a few exceptions, which will be described here. Like first component 80 of ISP 30, first component 180 of ISP 200, includes a lateral bone spacer 180a. Lateral bone spacer 180a has a center ring 180b. Center ring 180b forms a round opening 180c through which various substances, such as bone grafts or bone growth stimulating substances, may be passed through center ring 180b. Extending laterally in one direction from center ring 180b is superior bone anchor housing 182. Extending laterally in the exact opposite direction from center ring 180b is inferior bone anchor housing 182a. Both superior and inferior bone anchor housings 182 and 182a can be circular in shape for optimum anchoring capacity to the spinous process. In one embodiment, the superior and inferior bone anchor housings 182 and 182a are the same shape and size. In other embodiments, they are different shapes and/or sizes. In one embodiment, a straight line runs through the center of each of housings 182, 182a and center ring 180b, i.e., they are at an angle of 180° from one another as shown in FIG. 11.

Within each of housings 182 and 182a are self-aligning bone anchor assemblies 183 and 183a. Each of bone anchoring assemblies 183 and 183a contain one or more (four as shown in FIG. 11) spikes 184 and 184a that can penetrate bone. Spikes 184 and 184a protrude transversely in an inward direction from bone anchoring assemblies 183 and 183a. Spikes 184 and 184a are designed to penetrate the bone of the spinous process. While spikes 184 penetrate one spinous process, spikes 184a penetrate the next spinous process inferior to the one being penetrated by spikes 184. In addition, superior and inferior anchor housings 182 and 182a may be made of a unibody construction with center ring 180b, or alternatively, they may be secured to arms projecting from center ring 180b by pins or other means that permit superior and inferior anchor housings 182 and 182a to freely pivot at an angle relative to center ring 180b. Bone anchoring assemblies 183 and 183a are held within their respective housings 182 and 182a respectively by pins 193 and 193a. Pins 193 and 193a allow bone anchoring assemblies 183 and 183a to pivot within their respective housings 182 and 182a around an axis of rotation formed by pins 193 and 193a. Thus, bone anchoring assemblies 183 and 183a can pivot at an angle relative to housings 182 and 182a respectively as shown in FIG. 11. The maximum pivot angle is determined by the size of assemblies 183 and 183a relative to housings 182 and 182a. The greater the distance between the outer wall of assemblies 183 and 183a and the inner wall of their respective housings 182 and 182a, the greater the maximum pivot angle will be. The maximum pivot angle can be + or −1°, 2°, 3°, 4°, 5°, 6°, 7°, 8°, 9°, 10°, 11°, 12°, 13°, 14°, 15°, 16°, 17°, 18°, 19°, 20°, 21°, 22°, 23°, 24°, 25°, 26°, 27°, 28°, 29°, 30°, 31°, 32°, 33°, 34°, 35°, 36°, 37°, 38°, 39°, 40°, 41°, 42°, 43°, 44° or 45°. In one embodiment, the maximum pivot angle is + or − between about 1-10°. In another embodiment, the maximum pivot angle is + or − about 7°. As shown in FIG. 11, anchor assemblies 183 and 183a have axes of rotation that are perpendicular to one another, such that the axis of rotation of one of the assemblies is perpendicular to the axis of rotation of the other anchor assembly. In one embodiment, anchor assembly 183 pivots about a horizontal axis of rotation as shown in FIG. 11, while anchor assembly 183a pivots about a vertical axis of rotation as shown in FIG. 11. In another embodiment, anchor assembly 183 pivots about a vertical axis of rotation, while anchor assembly 183a pivots about a horizontal axis of rotation. However, pins 193 and 193a do not have to be aligned perpendicular to one another and they do not have to be horizontal and vertical. The pins can be aligned along the diameter of their respective anchor housings at any angle so long as the anchor assemblies 183 and 183a are able to pivot about the axis of rotation formed by the pins.

As with lateral spacer 80a of ISP 30, projecting transversely from the lateral bone spacer 180a and at a substantially 90° angle from lateral bone spacer 180a are two opposing zip lock flanges 187 and 187a, and two opposing bone abutments 186 and 86a. Alternatively, flanges 187 and 187a can be slightly biased inward toward each other for the purpose of forming a tight grip on barrel 197. A longitudinal axis extends from the center of center ring 180*b* to the distal ends of zip lock flanges 187 and 187*a* and bone abutments 186 and 186*a*. Zip lock flanges 187 and 187*a* are slightly rounded along their width forming the same arc as the circular center ring 180*b* from which they extend transversely. Zip lock flanges 187 and 187*a* are opposite each other and face each other as shown in FIG. 11. At the distal end of each of zip lock flanges 187 and 187*a* are one or more zip lock locking teeth 191 and 191*a* that protrude from the inward facing surfaces of the zip lock flanges 187 and 187*a*. FIG. 11 shows that flanges 187 and 187*a* have five zip lock teeth, but it can be fewer or more than that number of teeth. Each of zip lock teeth 191 and 191*a* form a top angled sliding face and a back locking ridge as shown in FIG. 11. The sliding face is angled to allow the teeth to slide forward and mate with the zip lock recesses or holes in second implant component 181. The back locking ridge of teeth 191 and 191*a* can form a substantially 90° angle with the zip lock flanges 187 and 187*a* or they can be angled toward the center ring 180*b* thus forming an acute angle between the back locking ridge and zip lock flanges 187 and 187*a*. If the angle is acute, then teeth 191 and 191*a* will be taller (i.e., they will extend further from their respective zip lock flange 187 and 187*a*) than when the angle is a substantially 90° angle for reasons that will be explained further below. The longer teeth will protrude through the recesses 190 and 190*a* at an angle thus creating a force that pulls second implant component 181 toward zip lock flanges 187 and 187*a* and prevents splaying the flanges 187 and 187*a* away from implant component 181. However, when the angle is substantially 90° and the walls forming the holes or recesses 190 and 190*a* are at 90°, then there is greater surface area contact between the back ridge of teeth 191 and 191*a* and the walls of recesses 190 and 190*a*, which increases the forces between teeth 191 and 191*a* and their respectively mated recesses 190 and 190*a*. The 90° configuration also reduces the risk of teeth breaking since the pressure on the back ridge is spread out across the entire surface area of the ridge rather than on just the narrow strip that makes contact with the edges of recesses 190 and 190*a*. Teeth 191 and 191*a* lock first and second components 180 and 181 longitudinally, radially, and transversely with respect to one another due to the forces between teeth 191 and 191*a* and recesses or holes 190 and 190*a* into which they slide. The outward facing surfaces of zip locking flanges 187 and 187*a* are substantially smooth. At the distal end of the top surface of each of zip lock flanges 187 and 187*a* are release nubs 194 and 194*a* respectively, which contain holes 195 and 195*a* respectively. A release tool can be inserted into each of holes 195 and 195*a* to bend flanges 187 and 187*a* away from barrel 197, thus pulling teeth 191 and 191*a* out of recesses 190 and 190*a* respectively. In on embodiment, as shown in FIG. 11, zip lock recesses 190 and 190*a* are elongated holes or slits that are shaped to receive teeth 191 and 191*a* respectively. In another embodiment (not shown in the figures) zip lock recesses 190 and 190*a* are formed by protruding teeth that extend radially outward from the barrel 197. Such teeth can be angled or sloped in the opposite direction of teeth 191 and 191*a* so that teeth 191 and 191*a* will slide over teeth 190 and 190*a* respectively when components 180 and 181 are forced into engagement with each other. When teeth 191 and 191*a* engage with teeth 190 and 190*a* respectively component 180 cannot be pulled apart from component 181, because the vertical back side of teeth 191 and 191*a* will catch against the vertical front side of teeth 190 and 190*a* respectively. In yet another embodiment, zip-lock recesses are formed by straight vertical protuberances over which teeth 191 and 191*a* slide. When teeth 191 and 191*a* engage with teeth protuberances 190 and 190*a* respectively component 180 cannot be pulled apart from component 181, because the vertical back side of teeth 191 and 191*a* will catch against the vertical protuberances 190 and 190*a* respectively.

Bone abutments 186 and 186*a* face each other and extend transversely from the inner side of lateral bone spacer 180*a*. As shown in FIG. 11, they are both slightly rounded along their width forming the same arc as the circular center ring 180*b* from which they extend transversely. Each of bone abutments 186 and 186*a* has a fusion window 185 and 185*a* respectively. Fusion windows 185 and 185*a* allow fusion between adjacent spinous processes through the barrel formed by the connection or mating between the first and second implant components 180 and 181. The outer facing surface of the bone abutments 186 and 186*a* may be smooth. Alternatively, they may be roughened to form more friction between bone abutments 186 and 186*a* and the spinous processes which they respectively abut. Increased friction will minimize any movement between the spinous processes and ISP 200 once ISP 200 is implanted between adjacent spinous processes.

Second implant component 181 mates with first implant component 180. Second implant component 181 has a lateral bone anchor 181*a* that faces and mirrors lateral bone spacer 180*a*. Lateral bone anchor 181*a* has a main function that is different than that of lateral bone spacer 180*a*. Whereas lateral bone spacer 180 has abutments 186 and 186*a* extending longitudinally to abut adjacent spinous processes and to keep the adjacent spinous processes separated from one another at a predetermined distance corresponding with the distance between the two bone abutments 186 and 186*a*, the primary purpose of lateral bone anchor 181 is not to have abutments extending from it, but to instead have a connecting barrel 197 extending transversely from it, which allows lateral bone spacer 180*a* and lateral bone anchor 181*a* to move toward or away from one another and to form a lock once the proper distance for anchoring to the spinous processes is determined.

Like lateral bone spacer 180*a*, lateral bone anchor 181*a* has a center ring 181*b*. Center ring 181*b* forms a round opening 181*c* through which various substances, such as bone grafts or bone growth stimulating substances, may be passed through center ring 181*b*. Extending laterally in one direction from center ring 181*b* is superior bone anchor housing 182*c*. Extending laterally in the exact opposite direction from center ring 181*b* is inferior bone anchor housing 182*d*. Both superior and inferior bone anchor housings 182*c* and 182*d* can be circular in shape for optimum anchoring capacity to the spinous process. In one embodiment, superior and inferior bone anchor housings 182*c* and 182*d* are the same shape and size. In other embodiments, they are different shapes and/or sizes. In one embodiment, a straight line runs through the center of each of housings 182*c*, 182*d* and center ring 181*b*, i.e., they are at an angle of 180° from one another as shown in FIG. 11.

Within each of housings 182*c* and 182*d* are self-aligning bone anchor assemblies 183*c* and 183*d*. Each of said bone anchoring assemblies 183*c* and 183*d* contain one or more (four in one embodiment) spikes that can penetrate bone. The spikes are the same as spikes 184 and 184*a*, and they protrude transversely from the inner side of bone anchoring assemblies 182*c* and 182*d*. The spikes are designed to penetrate the bone of the spinous process. While spikes extending from bone anchor housing 182*c* penetrate one spinous process, spikes extending from bone anchor housing 182*d* penetrate the next spinous process inferior to the one being penetrated by spikes extending from bone anchor housing 182*c*. In addition, superior and inferior anchor housings 182*c* and 182*d* may be made of a unibody construction with center ring 181*b*, or alternatively, they may be secured to arms projecting from center ring 181b by pins or other means that permit superior and inferior anchor housings 182c and 182d to freely pivot at an angle relative to center ring 181b. Bone anchoring assemblies 183c and 183d are held within their respective housings 182c and 182d respectively by pins 192 and 192a. Pins 192 and 192a allow bone anchoring assemblies 183c and 183d to pivot within their respective housings 182c and 182d around an axis of rotation formed by pins 192 and 192a. The bone anchoring assemblies can pivot at an angle relative to housings 182c and 182d respectively as shown in FIG. 11. The maximum pivot angle is determined by the size of assemblies 183c and 183d relative to housings 182c and 182d. The greater the distance between the outer wall of assemblies 183c and 183d and the inner wall of their respective housings 182c and 182d, the greater the maximum pivot angle will be. The maximum pivot angle can be + or −1°, 2°, 3°, 4°, 5°, 6°, 7°, 8°, 9°, 10°, 11°, 12°, 13°, 14°, 15°, 16°, 17°, 18°, 19°, 20°, 21°, 22°, 23°, 24°, 25°, 26°, 27°, 28°, 29°, 29°, 30°, 31°, 32°, 33°, 34°, 35°, 36°, 37°, 38°, 39°, 40°, 41°, 42°, 43°, 44° or 45°. In one embodiment, the maximum pivot angle is + or − between about 1-10°. In another embodiment, the maximum pivot angle is + or − about 7°. As shown in FIG. 11, anchor assembly 183c and 183d have axes of rotation that are perpendicular to one another, such that the axis of rotation of one of the assemblies is perpendicular to the axis of rotation of the other anchor assembly. In one embodiment, anchor assembly 183c pivots about a horizontal axis of rotation as shown in FIG. 11, while anchor assembly 183d pivots about a vertical axis of rotation as shown in FIG. 11. In another embodiment, anchor assembly 183c pivots about a vertical axis of rotation, while anchor assembly 183d pivots about a horizontal axis of rotation. However, pins 192 and 192a do not have to be aligned perpendicular to one another and they do not have to be horizontal and vertical. The pins can be aligned along the diameter of their respective anchor housings at any angle so long as the anchor assemblies 183c and 183d are able to pivot about the axis of rotation formed by the pins. Laterally on each side of the outer side of each of center rings 180b and 181b are indentations 188 (not visible on implant component 180), which receive a compression tool that is used to manipulate the ISP 200 during surgical procedures.

Center ring 181b has holes 189a and 189b that are arcuate and are shaped and sized to receive the distal ends of bone abutments 186a and 186 respectively. Holes 189a and 189b are opposite each other on the center ring 181b. When bone abutments 186a and 186 mate with holes 189a and 189b respectively, first and second components 180 and 181 are prevented from spinning relative to one another, and they become locked radially in place with respect to one another. Center ring 181b also has apertures 189c and 189d that form open rings that are each open at the top and are shaped and sized to receive the distal ends of zip lock flanges 187 and 187a respectively. The open ring configuration allows release nubs 194 and 194a to slide into the apertures 189c and 189d. Release nubs 194 and 194a are shaped to mate with apertures 189c and 189d.

Projecting transversely from the inner side of lateral bone anchor 181a and at a substantially 90° angle from lateral bone anchor 181a is barrel 197. Barrel 197 contains two columns of zip lock recesses 190 and 190a. Zip lock recesses 190 are opposite zip lock recesses 190a on the barrel 197. The column of zip lock recesses 190 is aligned with aperture 189c, and the column of zip lock recesses 190a is aligned with aperture 189d. Zip lock recesses 190 receive and mate with teeth 191 of zip lock flange 187, and zip lock recesses 190a receive and mate with teeth 191a of zip lock flange 187a. Barrel 197 also has window 197a and another window opposite it (not visible in FIG. 11). Window 197a and its opposite window (not visible) are the same size and shape as windows 185 and 185a and align with windows 185 and 185a respectively when components 180 and 181 are mated to one another.

First and second components 180 and 181 mate with one another in the following manner. As the two are brought toward one another, zip lock flanges 187 and 187a glide over the columns of zip lock recesses 190 and 190a of barrel 197. As the flanges 187 and 187a glide over barrel 197, bone abutments 186 and 186a glide over barrel 197 as well, and windows 185 and 185a become aligned respectively with window 197a and its opposite window of barrel 197. Barrel 197 thus becomes nested within bone abutments 186 and 186a and flanges 187 and 187a of first component 180, such that barrel 197 becomes radially nested within first component 180. Once windows 185 and 185a are aligned with window 197a and its opposite window respectively, a barrel is formed by the mating of component 180 and 181 with opposing windows (185 and 197a form one window while 185a and the window opposite 197a form another) through which bone can grow, such that bone from one spinous process can eventually fuse with bone from the adjacent spinous process through the windows. In addition, bone growth stimulating materials, such as natural or synthetic bone matrix or bone graft material, can be inserted through either of openings 180c or 181c into the barrel to help stimulate the growth of bone between the adjacent spinous processes.

When first and second components 180 and 181 are locked with one another through the mating of zip lock teeth 191 and 191a with zip lock recesses 190 and 190a respectively, anchor housings 182 and 182c are aligned opposite one another along a single longitudinal axis, and anchor housings 182a and 182d are aligned opposite one another along a single longitudinal axis.

First and second components 180 and 181 mate with one another to form a single ISP unit 200 that not only separates two adjacent spinous processes from one another at a predetermined distance, but keeps them locked with respect to one another as a result of the penetration of the spinous processes by the anchoring spikes (described above). Bone abutments 186 and 186a thus prevent extension between adjacent spinous processes, while the anchors prevent flexion between two adjacent spinous processes.

In one method of implantation, the assembled ISP 200 can be inserted between two spinous processes of adjacent vertebrae in an anterior to posterior direction after severing spinous ligaments to remove them from the path of implantation. In another method of implantation, no spinous ligaments are severed and the first and second components 180 and 181 are separated and can each individually be inserted from opposing lateral directions toward each other anterior to the undisturbed spinous ligaments. In any case, ISP 200 is inserted between two spinous processes of adjacent vertebrae. First and second components 180 and 181 are squeezed or pushed toward one another until the spikes on opposing anchor housings 182 and 182c penetrate the superior spinous process while the spikes on anchoring housings 182a and 182d penetrate the sides of the adjacent and inferior spinous process. With the penetration of the spikes the ISP 200 prohibits both extension (as a result of bone abutments 186 and 186a abutting the inner spinous process) and flexion (as a result of the anchoring by the spikes).

The locking mechanism described with respect to FIG. 11 is the mating of a series of teeth 191 and 191a with a series of recesses 190 and 190a respectively. This locking mechanism poses a significant advantage over previous locking mechanisms that use set screws, nuts or bolts. The use of a series of teeth creates forces that are significantly greater than can be achieved using a set screw, nut or bolt. Moreover set screws can come undone with time allowing the two parts of a spinal implant to slide apart from each other. The use of a series of zip locking teeth, such as in FIG. 11, prevents this problem. Moreover, disengagement of the described first and second components 180 and 181 from one another requires a two-step process: pulling the flanges apart from one another (a radial spreading force) while simultaneously pulling components 180 and 181 longitudinally away from one another (a longitudinal pulling or pushing force). The likelihood of both forces occurring at the same time inadvertently or through failure of the device over time are much lower than devices that use set screws, where the screw can become undone over time and then subsequent movement of the two parts away from each other can happen at a later time thus causing a failure of the device in situ. This type of locking mechanism is also a significant improvement over a simple ratchet, because a ratchet does not create the firm grip and increased forces created by the engagement of a series of successive teeth with a series of successive recesses.

Another important aspect of the embodiment depicted in FIG. 11 and described above is the ability of the anchor assemblies 183, 183a, 183c and 183d to pivot about an axis of rotation. This gives ISP 200 more flexibility and adaptability than it would otherwise have. It allows the anchor assemblies to orient themselves in an optimal angle toward the bone of the spinous process. Thus, the anchoring point of the spinous process does not have to be perfectly parallel with lateral bone spacer 180a and lateral bone anchor 181a in order for the spikes to form an optimal engagement with the spinous process, because the anchoring assembly can pivot to form a substantially parallel alignment with the bone thus forming the optimal surface area contact between the bone and the spikes.

FIGS. 12a-14f depict another embodiment of a non-dynamic interspinous fusion implant ("ISP") 300. ISP 300 is similar to ISP 200. It has the same zip-locking mechanism as ISP 200. The difference is that the inferior arms 382a and 382d do not have swiveling anchor assemblies. Instead they have spikes that project inwardly from sloped inward faces, while the superior arms do have the same swiveling anchoring assemblies as ISP 200. This different feature of ISP 300 makes it also particularly adapted for use in the sacral region like ISP 285. As shown in FIGS. 12a-12f, ISP 300 has superior arms 382 and 382c that face each other and have the same swiveling anchor assemblies as ISP 200. At the opposite, inferior end of ISP 300 are arms 382a and 382d that also face each other, but they do not have swiveling anchor assemblies. Instead, they have sloped faces and spikes extending transversely from the faces toward each other. Zip lock flanges 387 and 387a engage with two rows of opposing zip-lock recesses on barrel 397. This is the same as with zip-lock flanges 187 and 187a engaging with zip-lock recesses 190 and 190a respectively of ISP 200.

Like ISP 200, ISP 300 has two components: a first component 380 and a second component 381. First component 380 is shown in FIGS. 14a-14f. It has a lateral bone spacer 380a. Projecting in a superior direction from lateral bone spacer 380a is bone anchor housing 382. Projecting in an inferior direction from lateral bone spacer 380a is bone anchor housing 382a.

Each spinous process projects in a posterior direction from the lamina, such that the base of each spinous process is integral with the lamina and curves into the transverse process. The base of each spinous process is its thickest point and the spinous process tapers inward from the base to a midpoint and becomes thicker again at its posterior end. The bone anchor housings 382a and 382d are meant to be anchored to the base of the spinous process at its juncture with the lamina where it curves outward to form the transverse process, or with the sacrum which is also similarly sloped. To form a tight and continuous engagement with the base of the spinous process or the sacrum, the inward facing side of bone anchor housings 382a and 382d form a sloped faces 383a and 383d respectively. The slope of faces 383a and 383d is angled to match the angle at the base of spinous process (or sacrum) so that faces 383a and 383d are each in virtually continuous engagement with the bone at the base of the spinous process when implanted. Relative to a plane that runs perpendicular to barrel 397 and parallel with rings 380a and 381a, abutments 383a and 383d could form an angle of between about 0 degrees and about 45 degrees, i.e., that angle can be about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 degrees. Spikes 340a and 340d project inwardly from the abutments 383a and 383d respectively. As shown best in FIG. 13e, spikes 340d are substantially parallel with longitudinal axis x' of barrel 397 and are substantially perpendicular with a plane that runs perpendicular to barrel 397 and parallel with ring 381a. Likewise, as shown best in FIG. 14e, spikes 340a are substantially parallel with longitudinal axis x of flanges 387 and 387a and are substantially perpendicular with a plane that runs perpendicular to longitudinal axis x and parallel with ring 380a. As shown in FIGS. 13e and 14e, the longitudinal axes of spikes 340a and 340d form an acute angle with abutments 383a and 383d respectively. The angle and direction of the spikes 340a and 340d is important, because it results in a more secure transaction between the spikes and the bone of the sacrum. Spikes 340a project transversely from face 383a and they are perpendicular to the bone anchor housing 382a while forming an acute angle with face 383a. This configuration of a sloped face with perpendicular spikes provides a secure long-term engagement between the inferior end of the implant and the spinous process.

Extending transversely from bone spacer 380a are zip-lock flanges 387 and 387a and opposing bone abutments 386 and 386a, all of which project transversely from bone spacer 380a in the same direction. Zip-lock flanges 387 and 387a have already been discussed above. Bone abutments 386 and 386a are similar to bone abutments 186 and 186a, except that rather than forming a single window within each of the abutments, each abutment has a pair of windows separated by a pillar. Bone abutment 386 has windows 385-1 and 385-2 separated by pillar 385-3. Bone abutment 386a has windows 385a-1 and 385a-2 separated by pillar 385a-3. The windows allow for bone growth through the windows. The pillars 385-3 and 385a-3 strengthen the abutments 386 and 386a respectively. This improves the strength and rigidity of the abutment, particularly in wider implants that have longer abutments and flanges.

Second component 381 of ISP 300 is shown in FIGS. 13a-13f. Second component 381 has a lateral bone anchor 381a, the same as lateral bone anchor 181a of ISP 200. Projecting in a superior direction from lateral bone anchor 381a is bone anchor housing 382c. Projecting in an inferior direction from lateral bone anchor 381a is bone anchor housing 382d. Like bone anchor housing 382a, bone anchor housing 382d has sloped face 383d, which was described above.

Axis X-X extends transversely from bone spacer 380, and axis $X^1$-$X^1$ extends transversely from bone anchor 381. Those two axes meet when component 380 and component 381 are mated to one another. This coupling of component 380 and 381 is achieved in the same manner as the coupling of components 180 and 181 of ISP 200, and ISP 300 can be implanted in the same way as ISP 200 or ISP 30. When implanted, however, the inferior end of ISP 300 (i.e., anchor assemblies 382a and 382d) is engaged to the base of an inferior spinous process while the superior end (i.e., anchor assemblies 382 and 382c) is engaged to the posterior end of the spinous process just superior to the spinous process to which the inferior end of ISP 300 is engaged. Alternatively, ISP 300 is secured to the last spinous process and the sacrum such that the inferior end of ISP (ie., anchor assemblies 382a and 382d) is engaged to the sacrum while the superior end (i.e., anchor assemblies 382 and 382c) is engaged to the posterior end (or the laminal end) of the last spinous process in the vertebral column.

Figure 8A:
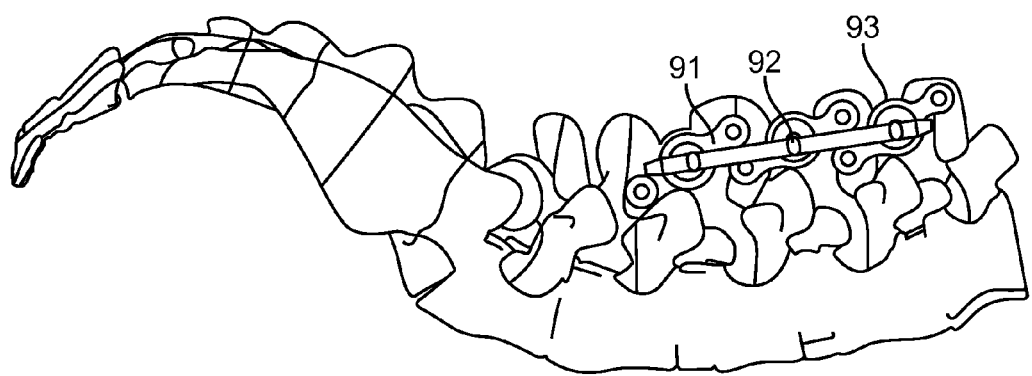
FIG. 8a is a side view of multiple successive interspinous implants implanted in the lumbar region of the vertrebral column in accordance with one embodiment in which the multiple implants are connected by a rod.

When stacking multiple ISP 300 implants, the order of implantation can be superior to inferior as this would be the most convenient order of implantation. This is shown in FIG. 8a. For example, ISP 93 would be implanted first, followed by ISP 92, then finally ISP 91. The superior end of ISP 93 is engaged to the posterior end of the most superior spinous process being treated while the inferior end is engaged to the base of the spinous process just inferior to the spinous process engaged by the superior end of ISP 93. Then the superior end of ISP 92 is engaged to the posterior end of the spinous process to which the inferior end of ISP 93 is engaged so that the superior end of ISP 92 is posterior to the inferior end of ISP 93. The inferior end of ISP 92 is engaged to the base of the next spinous process. Finally, the superior end of ISP 91 is engaged to the posterior end of the spinous process to which the inferior end of ISP 92 is engaged so that the superior end of ISP 91 is posterior to the inferior end of ISP 92. The inferior end of ISP 91 is engaged to the base of the next spinous process. This can be repeated with additional implants.

Figure 8B:
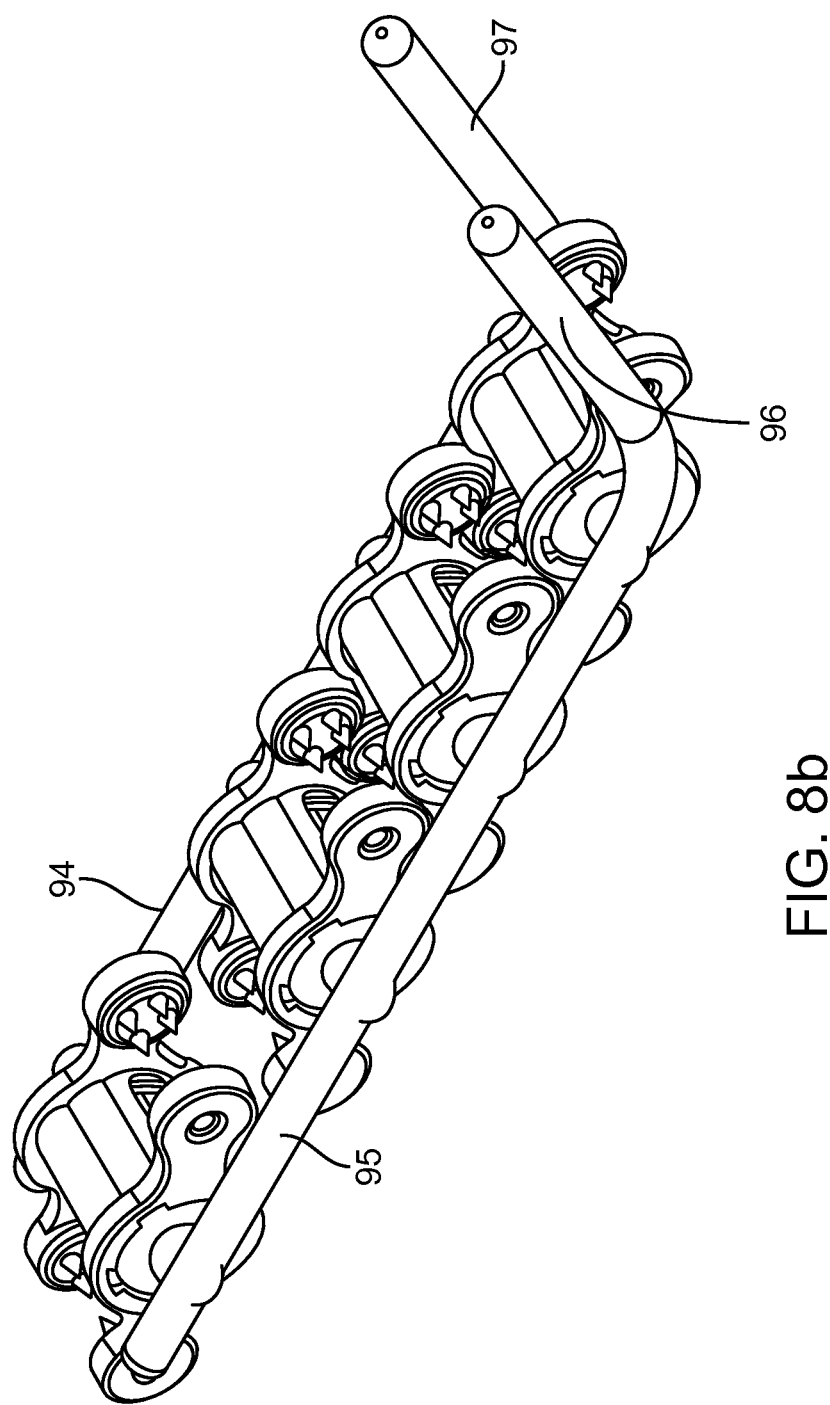
FIG. 8b is an isometric view of multiple successive interspinous implants connected to one another in a stack configuration by rods in accordance with one embodiment.

The stacked implants can be connected to one another for added stability and to aid the process of fusion using connecting rods 94 and 95 as shown in FIG. 8b. Connecting rods 94 and 95 are connected to opposing sides of the implants. Extensions 96 and 97 that curve outward can be added to the rods 95 and 94 respectively. Extensions 96 and 97 are connected to one or more plates secured to the base of the skull when the implants are implanted into the cervical spine.

Figure 8C:
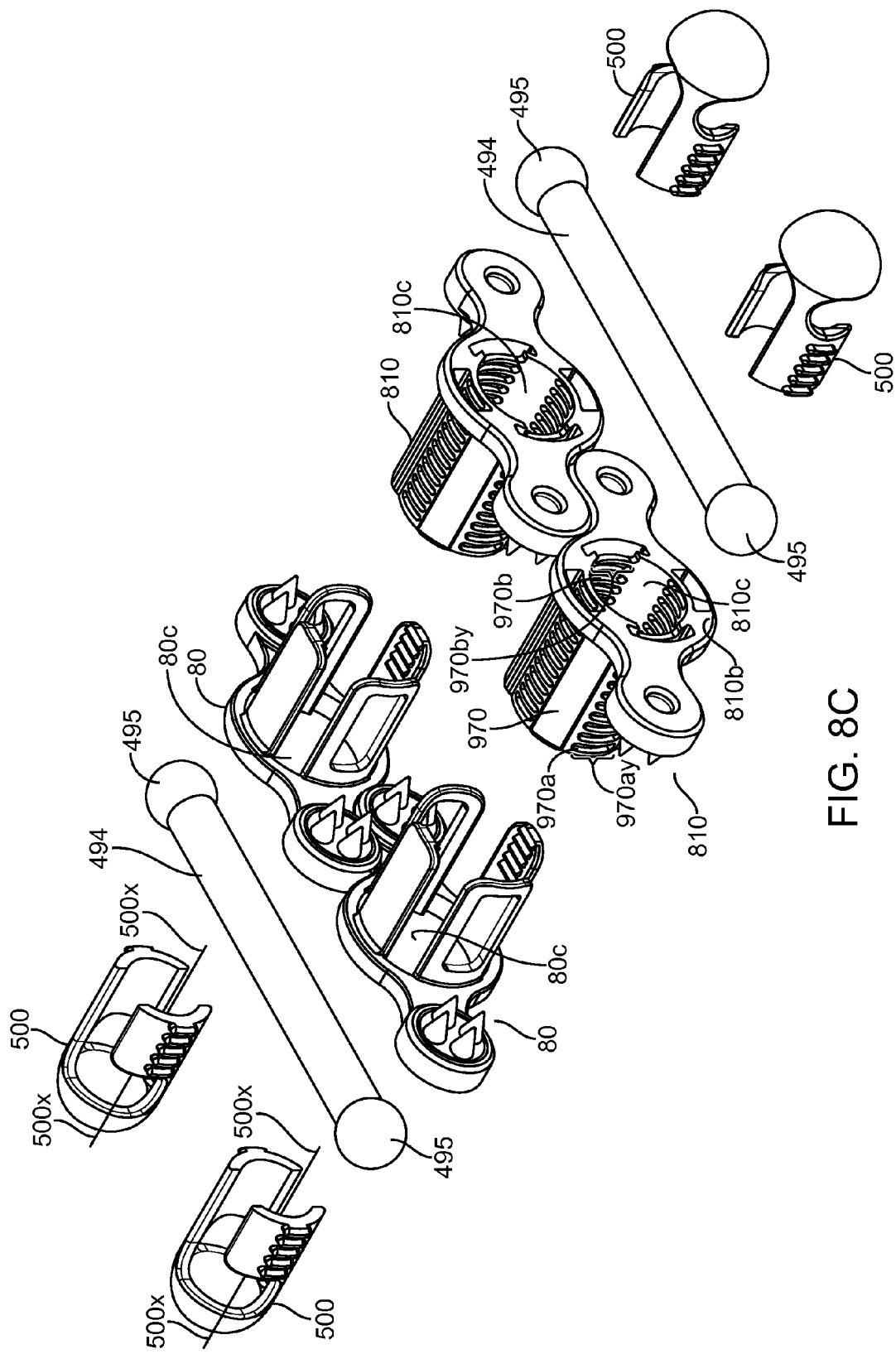

In FIG. 8c, a modified version of ISP 30 is used in which component 80 is the same as in ISP 30, but component 81 is modified so that windows 97a and 97b are replaced by ziplock recesses 970a and 970b. The stacked ISP assembly includes components 80 and 810, which mate with one another. In addition, there are a set of two rods 494. The two rods 494 are the same with each having a stop 495 at each of its ends. One of the rods 494 is assembled to components 80, while the other rod 494 is assembled to components 810. The rods 494 are held firmly in place with couplers 500. There is a set of two couplers 500 for each ISP unit. FIG. 8c depicts two ISP units, thus there are two sets of couplers 500 for a total of four couplers.

Figure 8D:
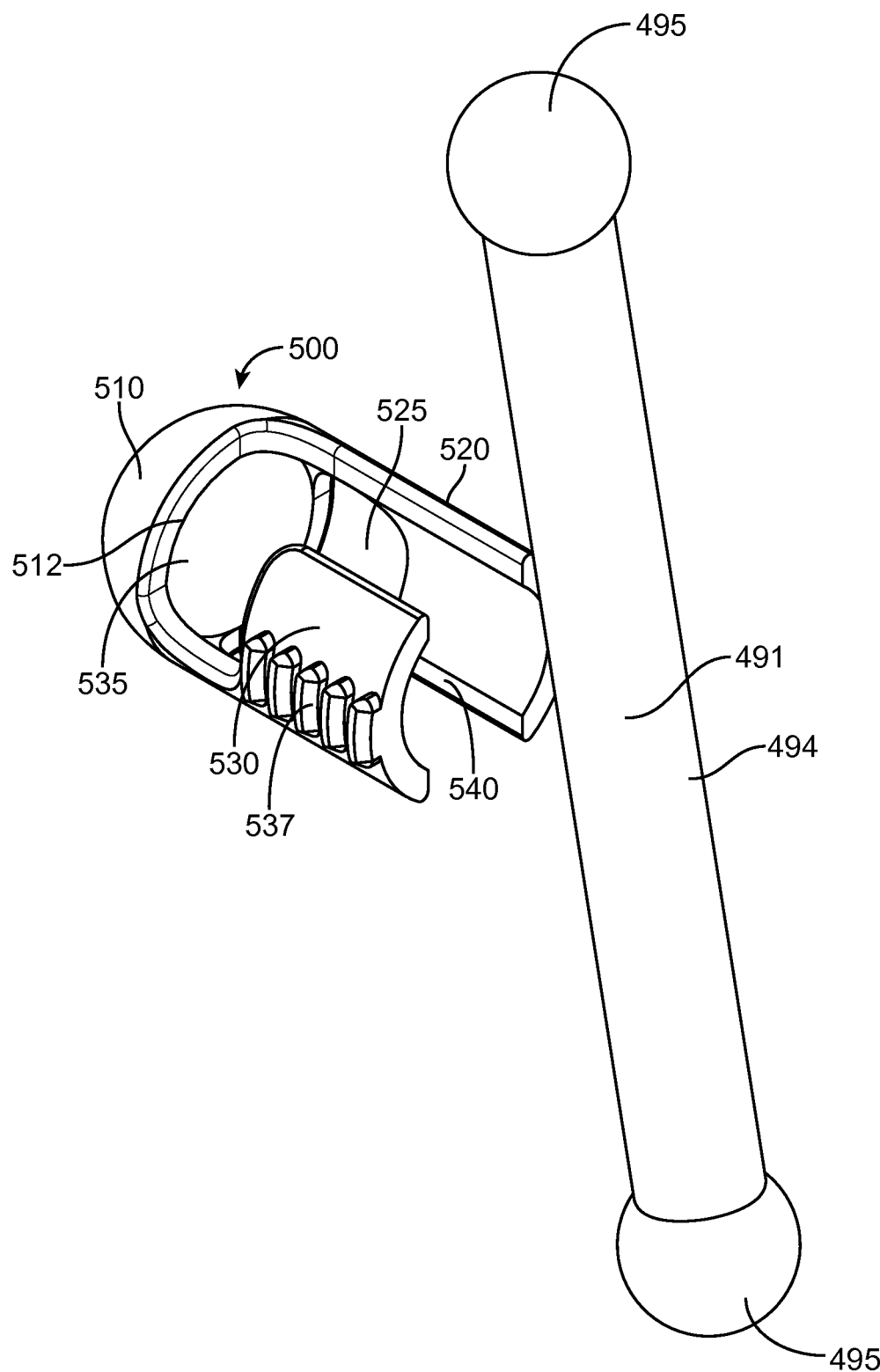
FIG. 8d is an exploded isometric view of the rod and nub assembly depicted in FIG. 8c.
Figure 8E:
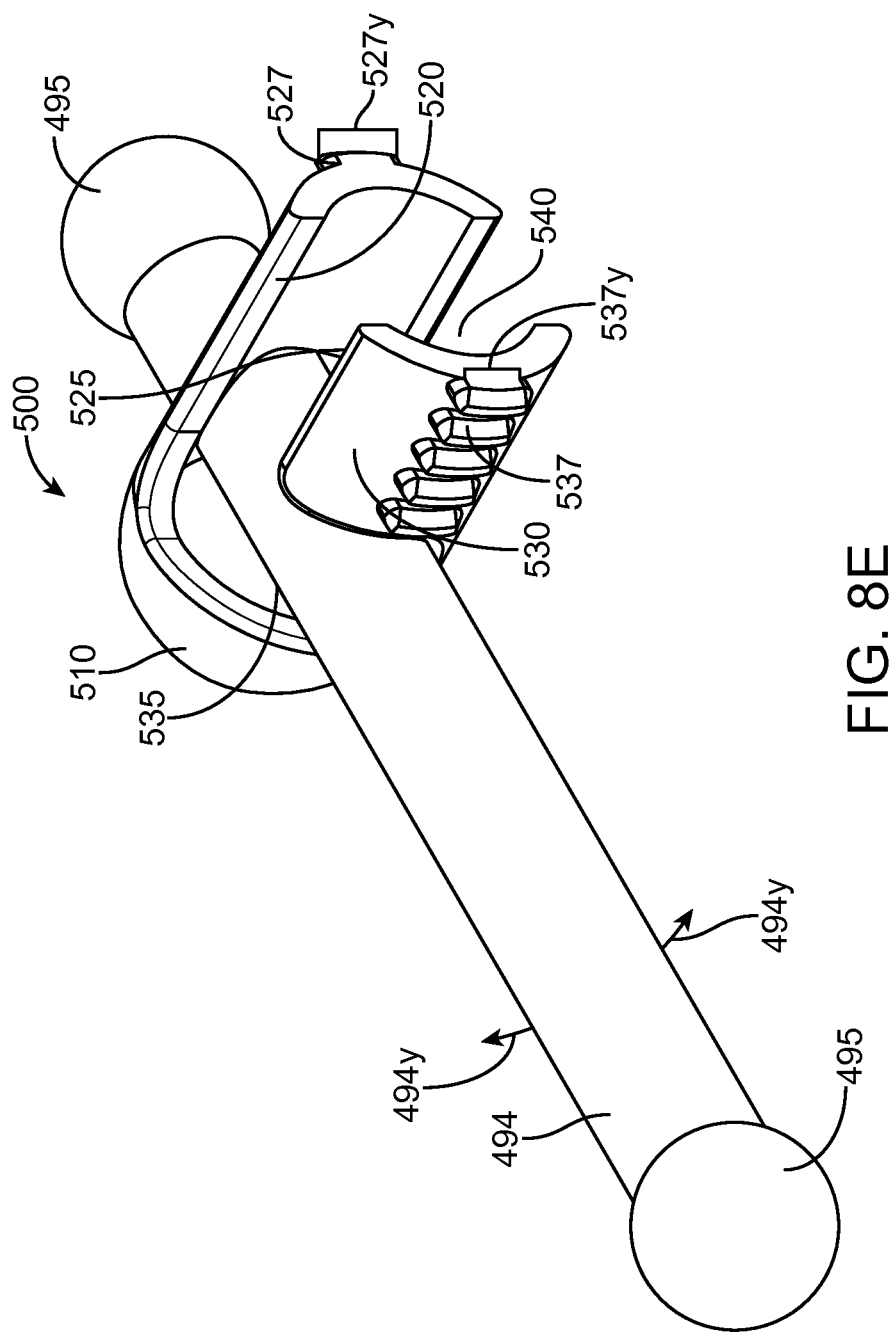
FIG. 8e is another isometric view of the rod and nub assembly depicted in FIG. 8d in a coupled state.
Figure 8F:
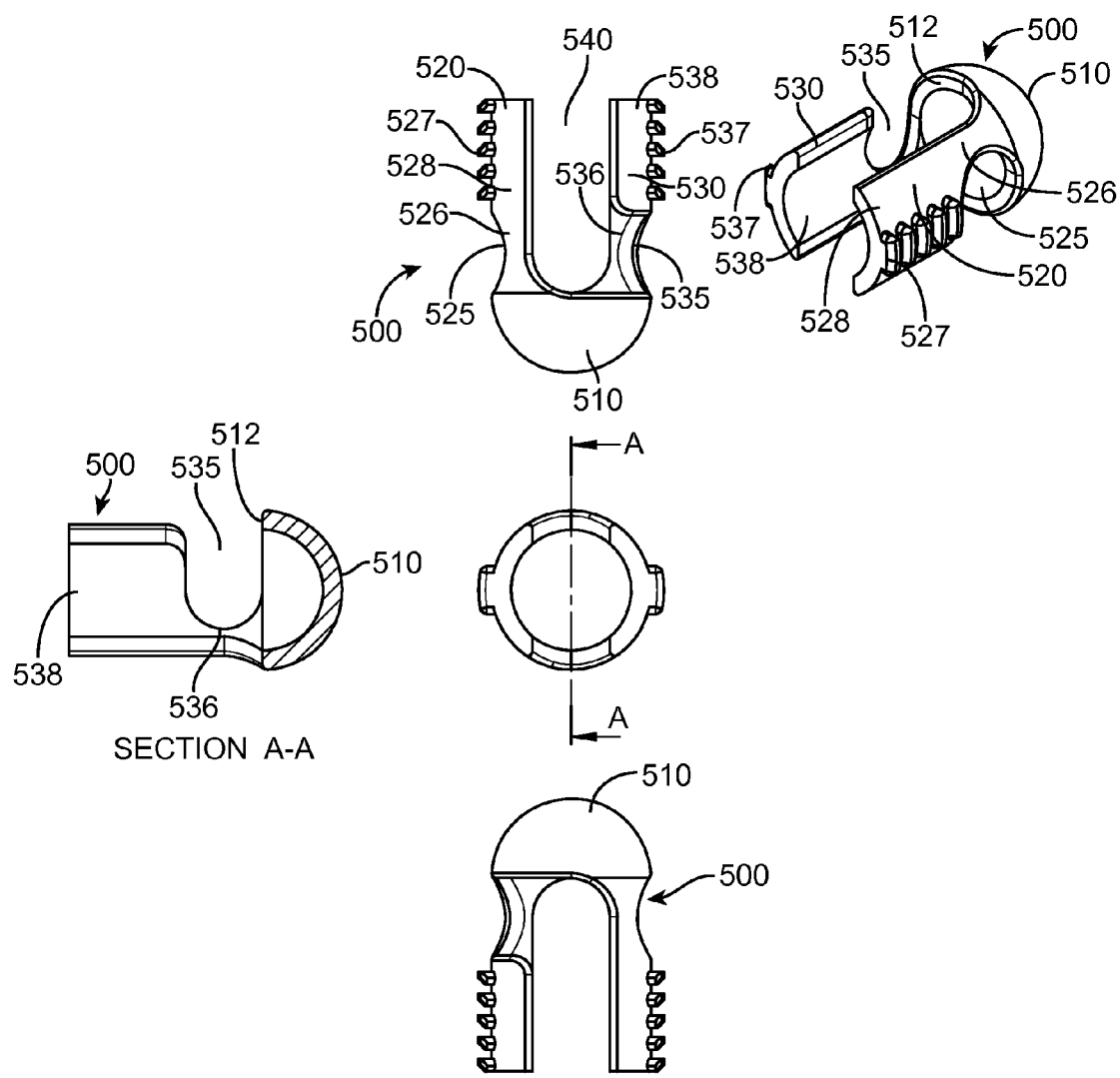
FIG. 8f provides several views of the nub depicted in FIGS. 8c-8e.

As shown in FIGS. 8d-8f, coupler 500 has a smooth rounded dome 510 forming its proximal end. Projecting transversely from dome 510 are two opposing arms 520 and 530, each with a proximal rod support section 526 and 536 respectively and an ISP lock section 528 and 538 respectively. The rounded dome 510 forms a circular rim 512 at its distal end. Rod support sections 526 and 536 extend distally from rim 512 so that arm 520 is connected (or integrally formed) to rim 512 through rod support section 526, and arm 530 is connected (or integrally formed) to rim 512 through rod support section 536. Rod support sections 526 and 536 are about 180° apart from one another along the circular rim 512. Rod support section 536 has an upward cutout section 535. Cutout section 535 forms a space between the rim 512 and the beginning or proximal end of the ISP lock section 538 that is sized to receive the rod 494. The cutout section 535 receives the rod 494. Rod support section 526 has a downward cutout section 525. Cutout section 525 forms a space between the rim 512 and the beginning or proximal end of the ISP lock section 528 that is sized to receive the rod 494, and it receives the rod 494. Arms 520 and 530 are arched to follow the arc formed by the rim 512. Arms 520 and 530 are separated from one another by channel 540. On the outer surface of lock sections 528 and 538 are zip-lock teeth 527 and 537 respectively. The teeth 527 and 537 are angled backwards, i.e., towards the proximal direction toward the dome 510. The top or distal surface of the teeth is sloped back, while the proximal or bottom surface of teeth 527 and 537 are at about a 90° angle with the outer surface of their respective lock sections 528 and 538. Thus, teeth 527 and 537 can slide forward through recessed holes, but cannot slide backward back out of recessed holes because of the vertical face of the proximal or bottom surface of teeth 527 and 537.

Each of the lock sections 528 and 538 importantly have not just one tooth 527 and 537 respectively but a series of teeth 527 and 537 respectively as shown in FIGS. 8c-8f. This is an important aspect, because the more teeth and corresponding recesses engage each other, the stronger the coupling that is formed. This is described and explained with respect to ISP 30 and ISP 200, and the same is true here with respect to the couplers 500, which are required to form a tight, secure, and long-term rigid coupling of the rods to the ISPs. In one embodiment, each of lock sections 528 and 538 has 2, 3, 4, 5, 6, 7, 8, 9, or 10 teeth. In one embodiment, lock sections 528 and 538 each have 5 teeth, and they mate with up to 5 recesses 970a that receive those teeth on barrel 970.

Rod 494 is inserted into multiple couplers 500 in the following manner. Rod 494 slides into a first coupler 500 through channel 540 until it rests against the rim 512. This is done with at least on additional coupler so that the rod 494 is coupled to at least two successive couplers 500 along its length.

Once a rod 494 is coupled to at least two couplers 500, the at least two couplers 500 can be coupled with the ISPs. This is done in the following way. Rods 494 can be coupled to components 80 and 810 in any order with 80 being first and 810 being next or vice versa. With respect to component 80, couplers 500 with assembled rod 494 are guided toward successive components 80 and the locking sections 528 and 538 of each coupler 500 are pushed through openings 80c of each successive ISP unit. Locking sections 528 and 538 of each coupler 500 slide through openings 80c of the ISPs. Teeth 527 come into contact with recesses 970a of barrel 970 of component 810. They slide into the recesses 970a and are able to be pushed forward through successive recesses because the top surface of the teeth are angled or sloped backward. The couplers 500 are pushed forward until the rod 494 is squeezed tightly between the rims 512 of each coupler and the center rings 80b of each ISP. The outer surface of center rings 80b and that of rod 494 can be rough or ribbed to maximize a friction lock between the rod 494 and rings 80b.

On the other side of the ISPs, another rod 494 is secured to components 810 in the same manner that rod 494 was secured to components 80. Once a rod 494 is coupled to at least two couplers 500 in the manner described above, the at least two couplers 500 can be coupled with multiple components 810 in the following manner. Couplers 500 with assembled rod 494 are guided toward components 810 and the locking sections 528 and 538 of each coupler 500 are pushed through openings 810c of each successive ISP unit. Locking sections 528 and 538 of each coupler 500 slide through openings 810c of the successive ISPs. Teeth 527 come into contact with recesses 970a of barrel 970. They slide into the recesses 970a and are able to be pushed forward through successive recesses because the top surface of the teeth are angled or sloped backward. The couplers 500 are pushed forward until the rod 494 is squeezed tightly between the rims 512 of each coupler and the center rings 810b of each successive ISP. The outer surface of center rings 810b and that of rod 494 can be rough or ribbed to maximize a friction lock between the rod 494 and rings 810b.

Before the rods 494 are firmly pressed against the ISPs by the couplers 500, the couplers 500 are designed to allow some adjustability so that the rods are aligned properly with the ISPs. The teeth 527 and 537 have a certain width 527y and 537y as best shown in FIG. 8e. The width 527y and 537y can be the same, but it is narrower than the width 970ay and 970by of the recesses 970a and 970b respectively. Thus, when teeth 527 engage with recesses 970a there is some free space between the ends of the teeth 527 and the sides of the recesses 970a. This is likewise the case with teeth 537 and recesses 970b with which they engage. The free space allows for the teeth to rotate within the recesses, and this allows the couplers 500 to rotate within the barrels 970 about axis 500x. This allows the rods 494 to tilt about arc 494y. Cutouts 535 and 525 also allow rod 494 to rotate through cutouts 535 and 525. Thus, the coupling system described herein allows flexibility to easily adjust the rods before they are tightly secured in place.

Rods 494 have stoppers 495 so that if rods 494 do slip, they will not fall out. The rods can be coupled to two, three, four or more successive ISPs. Rods 494 can come in various lengths. The shorter length rods can be used with two successive ISPs while longer rods can be used when additional ISPs are needed.

It is important that the rods be firmly secured and coupled to the ISPs. This is because the purpose of the rods is to minimize any movement between successive spinous processes. Stacking multiple ISPs and locking them together with rods provides the most rigid and non-dynamic means of fusion between successive vertebrae. Thus, if the desired result is fusion between successive vertebrae, it is preferable to eliminate as much movement between the successive vertebrae that are desired to be fused as possible. This aids the fusion process and hastens it. The rods coupled to successive ISPs eliminates as much movement between successive ISPs as possible and thus locks successive spinous processes together with respect to one another minimizing or eliminating any relative movement between those successive spinous processes. Thus, it is important to have a rod coupling system that is durable, long-term, convenient and easy to use while minimizing the risk of mechanical failure or slippage of the rods. The currently described zip-lock coupling system ideally achieves these objectives for the reasons described above.

Figure 9:
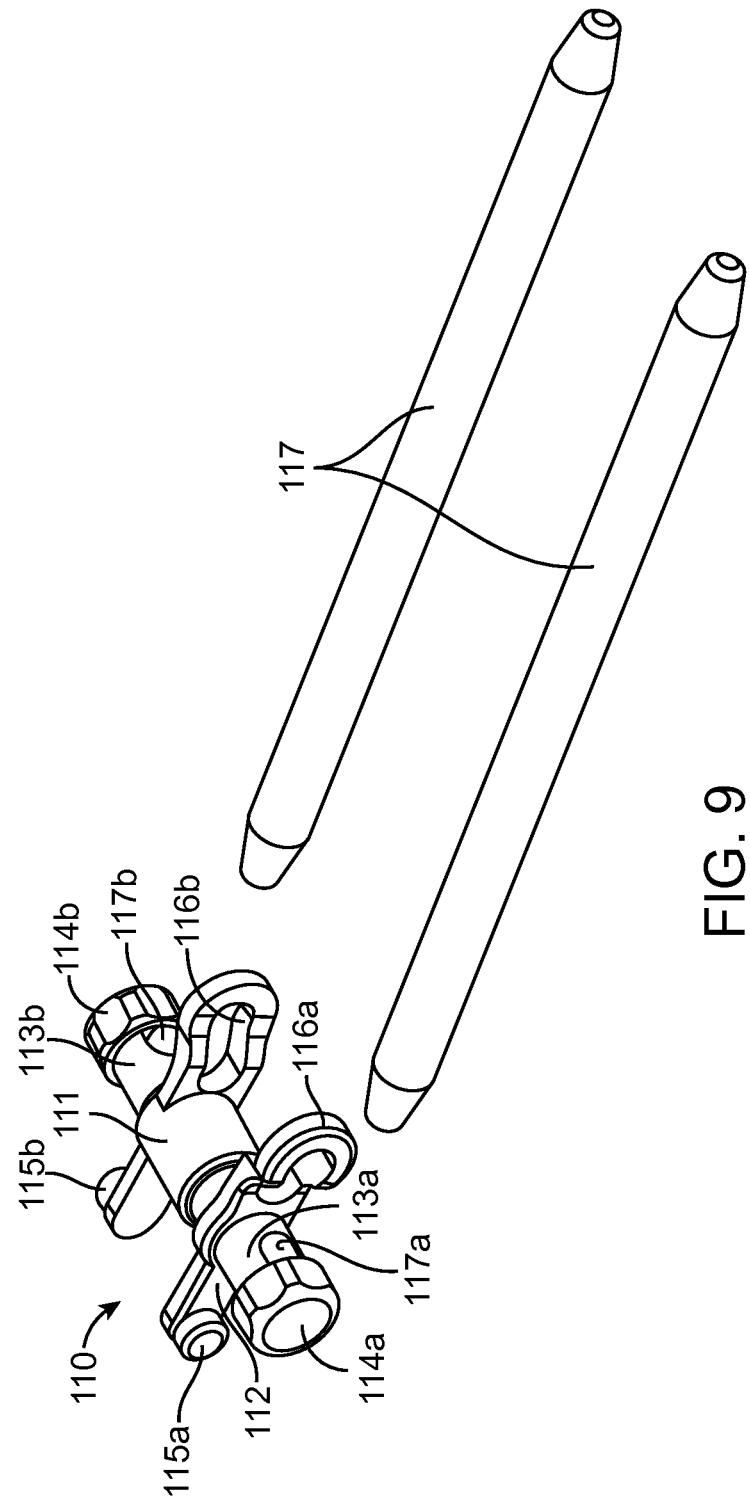
FIG. 9 is an exploded isometric view of an interspinous implant with connecting rods in accordance with another embodiment.

FIG. 9 depicts another embodiment of an ISP system that uses rods 117. The ISP system has an ISP 110 that has a component 111 and a component 112. Component 112 has a barrel that slides into a corresponding barrel on component 111. The barrels use a zip-lock locking mechanism with teeth projecting out from the barrel of one of the components fitting into teeth receiving recesses on the other barrel thus forming a lock between the barrels when the barrel of component 112 slides into the barrel of component 111. Component 112 has arms projecting laterally in a superior and inferior direction. Component 111 also has arms projecting laterally in a superior and inferior direction. One of the arms of component 112 has a nub 115a, while the other arm of component 112 has a hole 116a with an offset section. The hole 116a is sized to receive the nub 115a of another ISP 110. One of the arms of component 111 has a nub 115b, while the other arm of component 111 has a hole 116b with an offset section. The hole 116b is sized to receive the nub 115b of another ISP 110. Extending transversely in an outward direction from component 112 opposite its barrel is a rod receiver 113a that has a channel 117a that receives rod 117. The distal end of rod receiver 113a has a threaded section. Screw lock 114a is screwed onto the threaded section of rod receiver 113a until it comes into contact with rod 117 and squeezes rod 117 firmly in place inside channel 117a. Extending transversely in an outward direction from component 111 opposite its barrel is a rod receiver 113b that has a channel 117b that receives rod 117. The distal end of rod receiver 113b has a threaded section. Screw lock 114a is screwed onto the threaded section of rod receiver 113a until it comes into contact with rod 117 and squeezes rod 117 firmly in place inside channel 117a. Multiple ISPs 110 can be connected to another successively by coupling the nubs 115a and 115b of one ISP 110 to the holes 116a and 116b respectively of another ISP and thus stacking two, three, four or more ISPs along successive spinous processes. Channels 117a and 117b of the additional ISPs 110 can receive the rods 117 so that the rods form a rigid complex of ISPs. The barrel of component 112 can spin or rotate slightly within the barrel of component 111 so that the direction or angle of the rods along the spinal column can be adjusted. Alternatively, rod receivers 113a and 113b can rotate or spin about their axis independent of their respective barrels, thus allowing the direction or angle of the rods along the spinal column to be adjusted.

In another embodiment of the invention, an interspinous fusion implant ("ISP") 1000 system is shown in FIGS. 10a-10f. ISP system 1000 is adapted for implantation in the cervical spine and is highly modular and customizable. System 1000 is adapted to be used on multiple cervical spinal levels without the need for rods to connect successive implants. The components of the system 1000 include a barrel 1040 with an abrasive, roughened or ribbed surface finish to increases friction between it and components attached to it. In addition to the barrel 1040, there are hook members 1060 and 1061 that can be engaged with the barrel 1040. There are also connection plates 1030 to connect multiple barrels 1040 successively. In addition, there are screws 1020 that secure the plates 1030 to the barrels 1040.

ISP 1000 system is used in the following manner and is adapted to be used specifically in the cervical spine. Hook members 1060 and 1061 each have two regions. The first are barrel coupling regions formed by loops 1065 and 1067 respectively, and the second are lamina coupling regions formed by hooks 1064 and 1066 respectively. The loops 1065 and 1067 slide concentrically over barrel 1040. The inner surface of loops 1065 and 1067 can be abrasive, roughened or ribbed so that the loops 1065 and 1067 form a secure friction lock with 1040. The inner surface diameter of loops 1065 and 1067 are sized to match the outer surface diameter of barrel 1040, so that the barrel slides tightly through the loops 1065 and 1067.

Figure 10A:
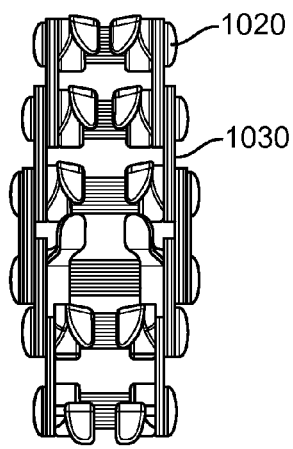
FIG. 10a is a top view of a modular cervical interspinous implant system in accordance with one embodiment.
Figure 10B:
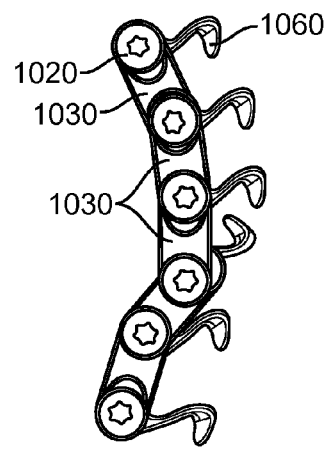
Figure 10C:
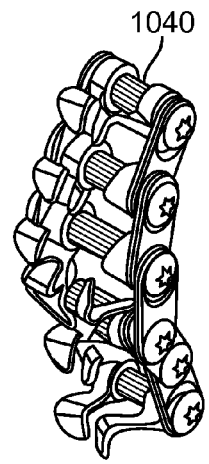
Figure 10D:
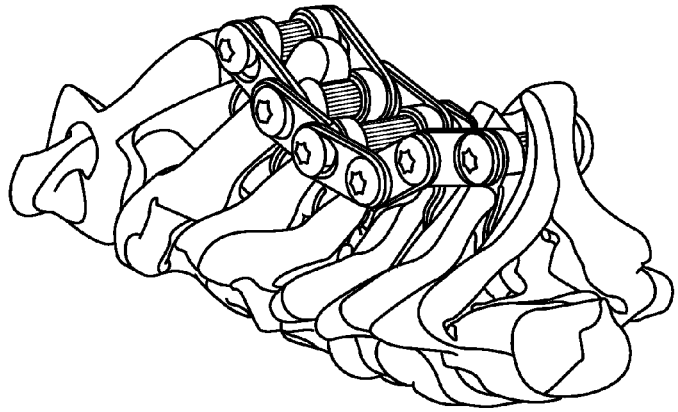
FIG. 10d is an isometric view of the modular cervical interspinous implant system depicted in FIG. 10a when implanted in the cervical region of the vertebral column.
Figure 10E:
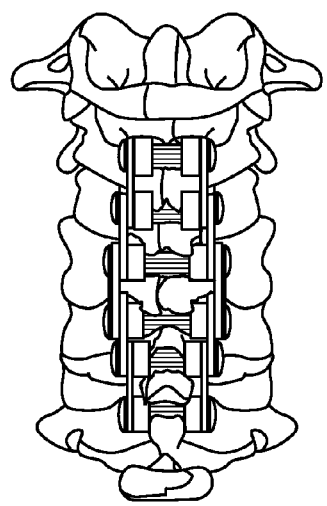
FIG. 10e is a top view of the modular cervical interspinous implant system depicted in FIG. 10a when implanted in the cervical region of the vertebral column.
Figure 10F:
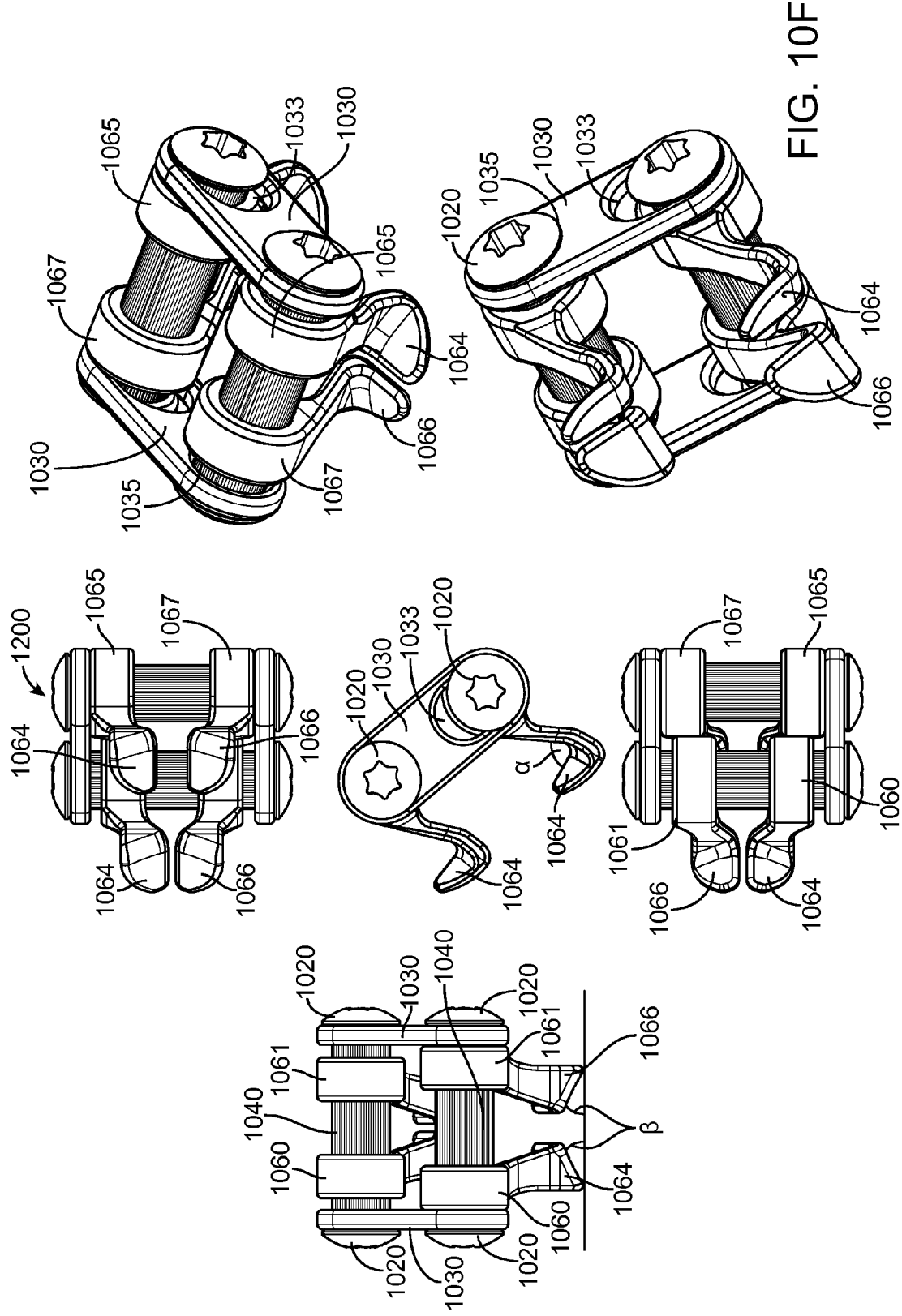
FIG. 10f provides various views of a cervical interspinous implant assembly in accordance with one embodiment.

Hooks 1064 and 1066 are adapted to engage the lamina of a cervical vertebra. Hooks 1064 and 1066 can be angled outward away from each other to match the angle of the lamina at its juncture with the spinous process. In one embodiment, hooks 1064 and 1066 form an acute angle α as shown in FIG. 10f. Angle α can be between about 60° and about 90°. In addition, the end of each hook 1064 and 1066 can be bent outward at an angle relative to a plane that is parallel with the barrel 1040 as shown in FIG. 10f. Angle can be between about 0° and about 60°, and in one embodiment it is between about 30° and about 45°.

Two hook members 1060 and 1061 are engaged with a first barrel 1040 to form a first cervical ISP subassembly. The hooks 1064 and 1066 of the hook members 1060 and 1061 respectively are each bent at an angle away from each other of between about 0° and about 60°, and in one embodiment between about 30° and about 45°, and in yet another embodiment at an angle of about 45°. Another two hook members 1060 and 1061 are engaged with a second barrel 1040 to form a second cervical ISP subassembly. Again hooks 1064 and 1066 of the hook members 1060 and 1061 respectively are each bent at an angle away from each other of between about 0° and about 60°, and in one embodiment between about 30° and about 45°, and in yet another embodiment at an angle of about 45°.

The two subassemblies are coupled together to form a cervical ISP assembly 1200 using lateral connection plates 1030. Each lateral connection plate 1030 has a pair of adjacent holes 1033 and 1035. Hole 1035 is circular and permits insertion of screw 1020 through it. Hole 1033 is oval and elongated compared to hole 1035, and it also permits insertion of screw 1020 through it. Screws 1020 are threaded and mate with threaded holes in the ends of barrels 1040. Hole 1033 permits screw 1020 to travel along the distance of oval hole 1033 when the screw isn't tightened down against plate 1030. Barrel 1040 has ends that have threaded holes in them that mate with the threaded screws 1020. Screws 1020 are inserted through holes 1033 and 1035 of a first plate 1030 and first plate 1030 is held against the first ends of two adjacent and parallel barrels 1040 so that threaded screws 1020 align with threaded screw holes in the first ends of the adjacent barrels 1040, and the screws are screwed into the threaded holes. Then two more screws are inserted through holes 1033 and 1035 of a second plate 1030 and the second plate 1030 is held against the other ends of the same two adjacent and parallel barrels 1040 so that the two additional threaded screws 1020 align with the threaded screw holes in the other ends of the adjacent barrels 1040, and the screws are screwed into the threaded holes. Screws 1020 that are inserted into holes 1035 and are tightened until the screw 1020 heads firmly squeeze the plates 1030 against the ends of the first barrel 1040. The second set of screws that are inserted through holes 1033 are not yet completely tightened until the device is assembly is implanted. This allows for adjustment between the subassemblies to account for each patient's unique anatomy and to account for the distance between successive spinous processes.

Once an ISP assembly 1200 is assembled, it can be implanted. Each barrel 1040 of the assembly 1200 is inserted between two successive spinous processes. The first set of hooks 1064 and 1066 engage with the lamina of a first vertebra by hooking in a downward direction over the lamina. The hooks 1064 and 1066 each are at an acute angle that forms a grip over the lamina. The corresponding barrel 1040 rests between the spinous process of the vertebra to which the hooks 1064 and 1066 have engaged and the spinous process of the vertebra just inferior to it forming an abutment between the two adjacent spinous processes. The second set of hooks 1064 and 1066 of the assembly 1200 engage with the lamina of the vertebra just inferior to the vertebra engaged by the first set of hooks in the same manner as the first set of hooks. The second barrel 1040 corresponding to the second set of hooks rests between the spinous process of the vertebra to which the second set of hooks 1064 and 1066 have engaged and the spinous process of the vertebra just inferior to it forming an abutment between those two adjacent spinous processes. Once the assembly 1200 is implanted the distance between the first and second barrels 1040 can be adjusted by moving the second barrel along the hole 1033 until just the right distance is achieved and then screwing the second set of screws 1020 against the plates 1030 and forming a tight squeeze between the plates 1030 and the second barrel 1040.

Another important feature of the assembly 1200 is that the hook members 1060 and 1061 can be independently rotated about the barrels 1040 by applying a strong force against the hooks 1065 and 1067. The independent rotation of each of the hook members 1060 and 1061 allows for significant variability in the implanted configuration of the assembly 1200 within the cervical spine. It allows the implant assembly 1200 to be maximally adaptable to the specific anatomy of the cervical spine of the patient who is receiving the implant. This is significant, because the vertebrae are not perfectly symmetrical, the lamina of the vertebra do not have perfectly predetermined shapes, and the distances between successive vertebra may be slightly variable. The adjustability of the hook members 1060 and 1061 through rotation about the barrels 1040 and the adjustability of the distance between the barrels 1040 is therefore an important feature of the assembly 1200.

Another important feature of ISP system 1000 is its modularity. The modularity of the system 1000 enables additional vertebra of the cervical spine to be engaged by adding additional subassemblies to the ISP assembly 1200. The assembly 1200 can expand from two barrels 1040 as shown in FIG. 10f to six or more barrels 1040 as shown in FIGS. 10a-10e. Additional barrels are added to the assembly 1200 using additional lateral connection plates 1030 and threaded screws 1020 to screw those plates 1030 against the barrels 1040. Multiple plates 1030 on opposite sides of the barrels 1040 can be used to connect together up to six or even more barrels 1040. As shown in FIGS. 10a-10e, in one embodiment, a stack of six barrels 1040 are connected to one another. In one embodiment, as shown in FIGS. 10a-10e, the hook members 1060 and 1061 on the third and fourth barrels can be oriented to face each other. This permits those hooks (on the third and fourth barrels 1040) to engage the same lamina from both the superior and inferior side of the lamina. With two sets of hooks latched onto a single lamina from both the top (superior) and bottom (inferior) side, the risk of the ISP system 1000 migrating or becoming detached from the cervical spine is minimized. In addition, the modularity of ISP system 1000 actually permits the hook members 1060 and 1061 to be turned to the other direction on any of the barrels 1040. This feature of engaging the hook members 1060 and 1061 in the opposite direction on the barrels 1040 allows the hooks 1064 and 1066 to have the flexibility to engage whichever lamina is better suited for engagement. Thus, if the inferior lamina is stronger, forms a better fit with the hooks 1064 and 1066 or some other anatomical feature makes it more suitable for engagement, the hooks 1064 and 1066 can be oriented on the barrel so that they are turned downward in the inferior direction to engage the inferior lamina. If, in contrast, the superior lamina is stronger, forms a better fit with the hooks 1064 and 1066 or some other anatomical feature makes it more suitable for engagement, then the hooks 1064 and 1066 can be oriented on the barrel so that they are turned upward in the superior direction to engage the superior lamina.

Yet another important feature of the ISP system 1000 is that it does not require bone engaging screws or rods. This minimizes the size of the implant and reduces both the incision and the amount of trauma experienced by the patient at the implant site, thus shortening recovery times and improving patient quality of life. Without pedicle screws that are screwed into the bone and rods connecting them, the trauma to the implant site is significantly reduced.

Another aspect of the present invention involves bone growth stimulation. Pulsed electromagnetic field therapy (PEMFT), also called pulsed magnetic therapy, pulse magnetotherapy, or PEMF, is a reparative technique most commonly used in the field of orthopedics for the treatment of non-union fractures, failed fusions, congenital pseudarthrosis and depression. In the case of bone healing, PEMF uses electrical energy to direct a series of magnetic pulses through injured tissue whereby each magnetic pulse induces a tiny electrical signal that stimulates cellular bone repair. It is believed that PEMF therapy causes biochemical changes at the cellular level to accelerate bone formation. In 1979 the FDA approved non-invasive devices using pulsed electromagnetic fields designed to stimulate bone growth. In 2004, a pulsed electromagnetic field system was approved by the FDA as an adjunct to cervical fusion surgery in patients at high risk of non-fusion.

Recent technologies in the field of promoting spinal fusion include capacitive coupling (CC) and combined magnetic field (CMF) devices. Both types of devices are worn externally and are used for up to nine months after spinal fusion surgery. CC stimulates a continuous biological response and is worn 24 hours per day. The device is made of two small, wafer-thin skin pads/electrodes that are placed directly onto skin over the fusion site. The CMF device delivers a time varying magnetic field by superimposing the time-varying magnetic field onto an additional static magnetic field.

Figure 15:
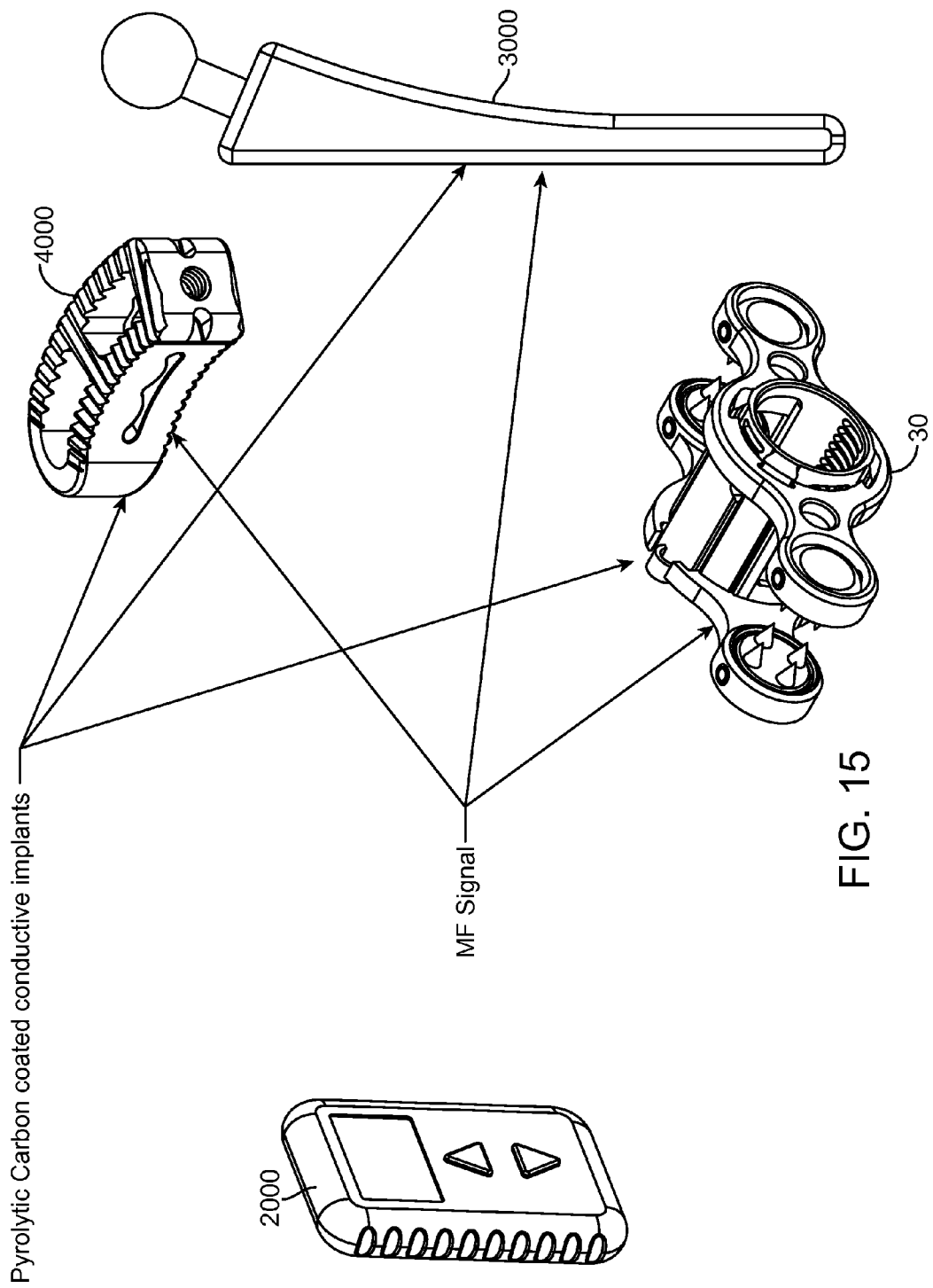
FIG. 15 is an illustration of a bone growth stimulation system.

What the current technologies lack are non-invasive means of direct bone growth stimulation precisely at the fusion site or orthopedic implantation site. One embodiment of the invention that addresses this shortcoming is depicted in FIG. 15, which shows a bone growth stimulation system using dual purpose implants. The implants are dual purpose in that they have a primary purpose of stabilizing a diseased skeletal region or replacing a bone or joint that has become irreparably injured. They also have a secondary purpose which is to aid in stimulating bone growth. The implants can be of any kind. For example, in FIG. 15, an intervertebral body or cage 4000, ISP 30 and an artificial femur 3000 are depicted. The implants can also be pedicle screws, plates, joints, or any other orthopedic implants.

Each of these implants is adapted to aid in bone growth in the regions in which they are implanted. Bone growth stimulation is achieved by making the implants of a specific material. Each of the implants is made of pyrolitic carbon or are coated with varying depths of a pyrolitic carbon surface. Previous orthopedic implants have been made of PEEK, PEKK, carbon fiber, silicon nitride, titanium alloys, trabecular and other metals. None have been adapted to be made of pyrolitic carbon and adapted to aid or stimulate bone growth.

Pyrolitic carbon is a structural carbon coating that is most often deposited on high density, high purity graphite pre-form. Other substrate pre-forms can also be used such as high melting point metals. The surface of pyrolitic carbon can be polished to a high gloss where articulation or thrombo-resistance is required. Alternatively, the surface can be left in an as deposited state providing some surface topography for bone and or tissue on-growth. Pyrolitic carbon is highly conductive and highly diamagnetic, making it an excellent material to receive a wireless signal, such as a radio-frequency or magnetic signal inducing it to emit a magnetic field.

As shown in FIG. 15, an external transmitter 2000 transmits a wireless signal to the ISP 30 (can also be ISP 200, ISP 285, ISP 300, system 1000 or assembly 1200 or any other implant disclosed herein), interbody vertebral spacer 4000 or femur implant 3000. Each of implants ISP 30 (can also be ISP 200, ISP 285, ISP 300, system 1000 or assembly 1200 or any other implant disclosed herein), interbody vertebral spacer 4000 or femur implant 3000 have a surface that is coated to varying depths of pyrolitic carbon deposited on a high purity graphite pre-form or another type of high melting point metal. The wireless signal transmitted by transmitter 2000 can be a magnetic frequency signal, a radio frequency signal, or any other type of wireless signal that can be received by implants ISP 30 (can also be ISP 200, ISP 285, ISP 300, system 1000 or assembly 1200 or any other implant disclosed herein), interbody vertebral spacer 4000 or femur implant 3000.

For example, in one embodiment, the external wireless transmitter communicates with interbody vertebral spacer 4000. Interbody vertebral spacer 4000 has dual functions. Its primary function is to be implanted between adjacent vertebrae and create space between those vertebrae. It has hollow openings into which bone growth material, such as synthetic or natural bone matrix, can be packed in order to aid in bone fusion between the two adjacent vertebrae. In addition, it has a pyrolitic carbon surface that can be smooth or porous. A porous surface will promote bone on-growth on the surface of the spacer 4000. During normal use it acts as a typical spacer. However, when it receives a wireless signal from the external transmitter 2000 the pyrolitic carbon surface acts as a conductor for that signal and it emits a magnetic field to the areas around it. The emission of magnetic field to the bone around the spacer 4000 stimulates bone growth of the native bone and enhances the activity of the packed bone matrix. Thus, spacer 4000 acts as a bone growth stimulator and promotes fusion when it is activated by the external wireless transmitter 2000.

The system described above with respect to FIG. 15 provides a significant improvement over prior systems that require external gear worn or placed on the skin to emit magnetic energy to skeletal tissue or removable leads implanted in the body and that extend out of the body, which need to be extracted after fusion is complete. The present system can remain in the body long-term, reduces the potential for infections do to leads extending out of the body, and eliminates the need for wearing bulky electromagnetic transmitters. In addition, devices like ISP 30, spacer 4000 and femur 3000 result in better and more efficient transmission of magnetic energy to the immediate substrate. Also the magnetic energy is emitted from the entire implant and radiates out from the implant in all directions rather than a unidirectional external transmitter. This results in better, more uniform, and more complete stimulation of the bone adjacent the implant.

In another example, the external wireless transmitter communicates with ISP 30 (this description applies equally to ISP 200, ISP 285 and ISP 300). ISP 30 has dual functions. Its primary function is to be implanted between adjacent spinous processes, create a space between them, stabilize the processes with respect to one another, and promote fusion between adjacent vertebrae. It has a hollow barrel (97 as shown in FIG. 4) into which bone growth material, such as synthetic or natural bone matrix, can be packed in order to aid in bone fusion between the two adjacent vertebrae. In addition, it has a pyrolitic carbon surface that can be smooth or porous. A porous surface will promote bone on-growth on the surface of the ISP 30. During normal use it acts as an interspinous fusion implant. However, when it receives a wireless signal from the external transmitter 2000 the pyrolitic carbon surface acts as a conductor for that signal and it emits a magnetic field to the areas around it. The emission of magnetic field to the bone around ISP 30 stimulates bone growth of the native bone and enhances the activity of the packed bone matrix. Thus, ISP 30 acts as a bone growth stimulator and promotes fusion when it is activated by the external wireless transmitter 2000.

Another problem addressed herein is that implants ideally should have a modulus of elasticity that is similar to the bone at the implant site. When an orthopedic implant is placed in the body to replace a bone or a part of a bone, it needs to handle the loads in the same way as its surrounding bone. If the modulus of elasticity of the implant is much greater than the modulus of elasticity of the native surrounding bone, the implant will take over the load bearing and the surrounding bone will start to decay. This will result in loosening of the implant and eventually ends in failure, the consequence of which is a revision surgery to replace the implant.

The present invention addresses the problem by providing kits of implants that contain varying ranges of modulus of elasticity. The implants used with the bone growth stimulation systems described herein can be packaged so that each kit or package includes a series of implants that each has a different modulus of elasticity. Thus, the kit includes implants of varying modulus of elasticity. The healthcare provider can determine the bone quality of each patient by performing a bone density scan at the implantation site and can then match an implant that has the nearest modulus of elasticity to the native bone at the implant site. In this way, the implant can be customized to match the bone density at the implant site of each patient, thus reducing the risk of reversion surgery.

For example, in one embodiment a kit can include the following implants, tools and materials: (1) an ISP 30 having a modulus of elasticity of between about 5 GPa and about 15 GPa (e.g., about 10 GPa in one embodiment); (2) an ISP 30 having a modulus of elasticity of between about 15 GPa and about 25 GPa (e.g., about 20 GPa in one embodiment); and (3) an ISP 30 having a modulus of elasticity of between about 25 GPa and about 35 GPa (e.g. about 30 GPa in one embodiment). In one embodiment, the kit can also include (1) an ISP 30 having a modulus of elasticity of between about 35 GPa and about 45 GPa (e.g., about 40 GPa in one embodiment); (2) an insertion/compression tool; (3) a removal/splaying tool; (4) synthetic or natural bone matrix, such as bone matrix pellets; (5) a wireless signal transmitter; and (6) instructions for use. In another embodiment, a kit can have all of the materials set forth above plus the following: (1) additional sets of ISPs 30 at each modulus of elasticity for the purpose of stacking ISPs for multiple implantation; (2) rods (such as rods 494) for connecting the multiple ISPs 30; and (4) couplers (such as couplers 500) for coupling the rods to the ISPs 30.

In yet another example, a kit can include the same elements as set forth above, except that each of the ISPs 30 are replaced with spacers 4000 in which each of the spacers has the same modulus of elasticity as the ISPs 30 in the above described kit.

In yet another example, a kit can include the same elements as set forth above, except that each of the ISPs 30 are replaced with a femur implant 3000 in which each of the femur implants has the same modulus of elasticity as the ISPs 30 in the above described kit.

While the invention is susceptible to various modifications and alternative forms, specific examples thereof have been shown by way of example in the drawings and are herein described in detail. It should be understood, however, that the invention is not to be limited to the particular forms or methods disclosed, but to the contrary, the invention is to cover all modifications, equivalents, and alternatives falling within the spirit and scope of the appended claims.

We claim:

1. An interspinous fusion device comprising:
   a first member having a ring with two or more anchor assemblies projecting laterally from substantially opposite sides of said first member ring, the first member further comprising a first flange and a second flange that each extend transversely and from opposite sides of the ring, the two flanges facing each other and biased toward one another, wherein each of said first and second flanges comprises a series of teeth protruding inwardly therefrom;
   a second member having a ring with two or more anchor assemblies projecting laterally from substantially opposite sides of said second member ring, the second member further comprising a barrel extending transversely from the second member ring wherein the barrel comprises a first column of recesses adapted to mate with the teeth of the first flange and a second column of recesses adapted to mate with the teeth of the second flange, wherein the barrel has openings on opposite sides of the barrel in between the first and second column such that when the first member is mated with the second member there are no other mechanical components within the barrel such that an unobstructed passage is formed through which bone graft material can extend;
   wherein the first member is adapted to slide over the barrel of the second member such that the series of teeth of the first flange mates with the recesses in the first column of recesses of the barrel and the series of teeth of the second flange mates with the recesses in the second column of recesses of the barrel, the bias of the two flanges further causing the two flanges to compress down onto the barrel to form a compression lock with the barrel without the aid of a set screw, a pin, or other mechanical component.

2. The interspinous fusion device of claim 1, wherein the second member further comprises a first bone abutment and a second bone abutment, each of said first and second bone abutments extending transversely from the first member ring.

3. The interspinous fusion device of claim 2, wherein each of said bone abutments has an opening formed on its respective surface.

4. The interspinous fusion device of claim 3, wherein the barrel comprises a first opening and a second opening on its surface, wherein the openings on the abutments can be substantially aligned with the openings on the barrel when the spacer member is secured to the anchor member through the mating of the teeth of the flanges to the recesses of the barrel such that a continuous opening extends through the barrel in which no other mechanical components are within the barrel.

* * * * *